(12) United States Patent
Nozaki et al.

(10) Patent No.: US 7,315,785 B1
(45) Date of Patent: Jan. 1, 2008

(54) METHOD AND SYSTEM FOR DISPLAYING DENDROGRAM

(75) Inventors: Yasuyuki Nozaki, Kanagawa (JP); Tsunehiko Watanabe, Kanagawa (JP); Ryo Nakashige, Kanagawa (JP); Takuro Tamura, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 09/890,929

(22) PCT Filed: Nov. 17, 2000

(86) PCT No.: PCT/JP00/08133

§ 371 (c)(1),
(2), (4) Date: Aug. 7, 2001

(87) PCT Pub. No.: WO01/45026

PCT Pub. Date: Jun. 21, 2001

(30) Foreign Application Priority Data

Dec. 14, 1999 (JP) .................................. 11-354401

(51) Int. Cl.
*G06F 19/00* (2006.01)
(52) U.S. Cl. ........................................................ 702/19
(58) Field of Classification Search .................. 702/19
See application file for complete search history.

(56) References Cited

U.S. PATENT DOCUMENTS 5,065,347 A 11/1991 Pajak et al.
5,895,474 A 4/1999 Maarek et al.

FOREIGN PATENT DOCUMENTS

| JP | 2-14873 | 11/1988 |
| JP | 2-226380 | 2/1989 |
| JP | 7-85099 | 9/1993 |
| WO | WO 99/09218 | 2/1999 |

OTHER PUBLICATIONS

Swayne et al. (Journal of Computational and Graphical Statistics (1998) vol. 7, No. 1, pp. 1-19).*
Michaels et al. (Pacific Symposium on Biocomputing (1998) vol. 3, pp. 42-53).*
Ludwig, et al., "A Software Environment for Sequence Data", Technisch Universitat Munchen, Lehrstuhl fur Mikrobiologie, Apr. 16, 1997, pp. 1-43.
Eisen, et al., "Cluster Analysis and Display of Genome-wide Expression Patterns", Proc. Natl. Acad. Sci., USA, vol. 95, pp. 14863-14868, Dec. 1998.
Sadao Ishida, "Procedure for Multivariate Data Analysis by SPSS", Apr. 24, 1998, pp. 172-181.
M.B. Eisen, P.T. Spellman et al., "Cluster Analysis and Display of Genome-Wide Expression Patterns", Proceeding of the National Academy of Sciences, Dec. 1998, vol. 95, pp. 14863-14868.

* cited by examiner

*Primary Examiner*—Lori A. Clow
(74) *Attorney, Agent, or Firm*—Reed Smith LLP; Stanley P. Fisher, Esq.; Juan Carlos A. Marquez, Esq.

(57) ABSTRACT

The present invention represents a global state of branches in a whole dendrogram as well as detail of states of individual subtrees, to aid focusing of groupings and selection of a clustering method. The present invention selects a branch/subtree in a dendrogram displays the subtree on a separate window, replaces the subtree with an icon then restores the icon into the original subtree, and/or searches keywords contained in information of biopolymers in the subtree then highlight the locations of biopolymers containing the keywords in its information.

15 Claims, 18 Drawing Sheets

Furthest neighbor method

Nearest neighbor method

Distance (dissimilarity) between clusters

Distance (dissimilarity) between clusters

Fig. 11 gene_info

| | Member | Value |
|---|---|---|
| 1101 | geneID | 17 |
| 1102 | ORF | YBL084C |
| 1103 | name | ANAPHASE-PROMOTING COMPLEX SUBUNIT |
| 1104 | function | CELL CYCLE |

Fig. 12 cluster

| | Member | Value |
|---|---|---|
| 1201 | type | leaf |
| 1202 | left | |
| 1203 | right | |
| 1204 | distance | |
| 1205 | clusterNo | 17 |
| 1206 | geneID | 11 |
| 1207 | windowID | 3 | cluster

| Member | Value |
|---|---|
| type | node |
| left | 153 |
| right | 17 |
| distance | 91 |
| clusterNo | 328 |
| geneID | |
| windowID | 3 | cluster

| Member | Value |
|---|---|
| type | icon |
| left | 256 |
| right | |
| distance | |
| clusterNo | 419 |
| geneID | |
| windowID | 3 |

METHOD AND SYSTEM FOR DISPLAYING DENDROGRAM

FIELD OF THE INVENTION

The present invention relates to a method and a system for displaying data (gene expression data) obtained by hybridization with a specific biopolymer such as a gene, in a visually comprehensible format so that functions and roles of the biopolymer (gene) can readily be studied.

BACKGROUND OF THE INVENTION

With the increase in the number of species that have been determined of their genome sequences, so called genome comparison has extensively been performed. Genome comparison aims at finding facts based on gene differences among species, for example, finding genes involved in evolution, finding a collection of genes which are considered to be common to all species, or, conversely, studying the nature unique to specific species. The recent development of infrastructures such as DNA chips and DNA microarrays has changed the interest in the art of molecular biology from information of interspecies to information of intraspecies, namely coexpression analysis, and broadened the study covering from extraction of information to correlation of information, including the conventional comparison between species.

For example, if an unknown gene has an expression pattern identical to that of a known gene, the unknown gene can be assumed to have a similar function to that of the known gene. Functional meanings of such genes and proteins are studied as function units or function groups. The interactions between the function units or function groups are also analyzed by correlating with known enzymatic reaction data or metabolism data, or more directly, by knocking out or overreacting a specific gene to eliminate or accelerate expression of the gene in order to study the direct and indirect influences on gene expression patterns of a whole collection of genes.

One successful case in this field would be the expression analysis of yeast by the group of P. Brown et al. from the Stanford University (Michel B. Eisen et al., Clustering analysis and display of genome-wide expression patterns, *Proc. Natl. Acad. Sci.* (1998), Dec 8; 95(25): 14863-8). They conducted hybridization of genes extracted from a cell in a time series using a DNA microarray, and numerated the expression levels thereof (i.e., numerated the brightness of the hybridized fluorescent signals). Based on the numerated values, genes having similar expression patterns in their gene cycles (genes having closer expression levels at some point) are clustered together.

FIG. 1 is a diagram showing an exemplary display for showing similarity between expression patterns of genes according to the above-mentioned system. Information of each of the observed genes is listed on the right hand side, and a dendrogram formed based on the expression patterns of these genes is drawn on the left hand side. The dendrogram is drawn by stepwise joining every two most similar clusters together. The length of each branch corresponds to the distance (dissimilarity) between the two joined clusters. This displaying method allows a supposition that genes belonging to the same cluster may possibly share common functional characteristics.

In an actual analysis of gene expression patterns, a enormous amount of data will be subjected to clustering. A DNA chip or DNA microarray is usually capable of detecting thousands to ten-thousands of genes at the same time. Generally, an expression of one gene may induce or inhibit an expression of another gene, forming a complicated network among genes. Therefore, if the numbers of genes to be observed are larger, more complicated and detailed gene network can be studied.

However, as the number of genes is increased, it becomes very difficult to find the functions of the entire genes. Since a dendrogram will represent several thousands to ten-thousands of genes, it is difficult from the display to judge what kind of grouping has been made. Furthermore, the lengths of branches in the resulting dendrogram generally differ depending on the type of clustering method employed. For example, when a furthest neighbor method is employed as a cluster combining algorithm, the average length of the branches will be longer than the average length of branches resulting from a nearest neighbor method. Therefore, looking at overall dendrograms in FIG. 2, a length from a root to leaves also varies depending on the clustering method. For clustering gene expression data, it is more important to find out the groupings than to observe the lengths of the branches. Accordingly, as shown in FIG. 3, a dendrogram is generally displayed while a length from the root to the leaves of the dendrogram is fixed in advance. As a result, lengths of the branches are determined relative to the length of the whole dendrogram and a scale of the lengths of the branches differs depending on the clustering method.

According to the above-described method for displaying a dendrogram, when the dendrogram contains numbers of genes having similar expression patterns, the lengths of the branches will be short. When the lengths of these branches are too short relative to the length of the dendrogram, it becomes very difficult to find detailed relationship between the branches of genes as can be appreciated from a range 401 in FIG. 4. According to a conventional clustering for a gene expression analysis, an interactive operation such as selecting a subtree and then subjecting the selected subtree to another clustering method, was impossible. Moreover, according to a conventional clustering for a gene expression analysis, whether the grouping was successful or not is confirmed by focusing on the functions of genes or keywords derived from gene names to see whether relative genes are assembled in a subtree. However, when the number of genes to be analyzed is numerous, it is difficult to determine which function or keyword should be focused on.

The present invention aims at solving such conventional problems, and has an objective to provide a method and a system for displaying a dendrogram such that the state of branches of the whole dendrogram can globally be understood, and such that a detailed state of each subtree can be studied.

SUMMARY OF THE INVENTION

In order to achieve the above-mentioned objective, the present invention proposes a system for displaying a dendrogram which is provided with functions for selecting a branch in a dendrogram, displaying a subtree extending from the selected branch to the downstream leaves on a separate display window, replacing the subtree with an icon, restoring the icon to the subtree, and collecting and displaying keywords contained in the subtree. According to the present invention, subtrees of a produced dendrogram can be subjected to different clustering methods interactively. Keywords contained in the subtrees can be displayed in order to confirm success of clustering as well as to aid focusing of groupings and to aid selection of a clustering method.

Hereinafter, exemplary dendrogram displays according to a dendrogram displaying system of the invention will be described. Herein, for clearer understanding, the invention is applied to a case of genes, although the application of the present invention is not limited to genes. The present invention can equally be applied to other biopolymers such as cDNAs, RNAs, DNA fragments or the like.

FIG. 5 is a view showing an exemplary display of a dendrogram resulting from a dendrogram displaying system of the invention. The display includes a grouping algorithm selection menu 501 and a (dis)similarity selection menu 502. A dendrogram is produced by reading out gene expression data, and selecting a grouping algorithm and a type of (dis)similarity. The present system may also be capable of displaying gene information next to the leaves of the dendrogram as shown in FIG. 1.

By selecting a branch in the produced dendrogram, a subtree extending from the selected branch to the downstream leaves can be made the subject of operations. Specifically, the subtree can be displayed on a separate window; the subtree can be replaced with an icon; the icon can be restored to the subtree; and keywords contained in the subtree can be searched. These operations can be selected from the menu. In the figure, a branch 505 in the middle of the screen is selected with a mouse cursor 504 or the like represented by an arrow, upon which a menu window 503 appears on which selectable operations are displayed. By transferring the mouse cursor 504 to a desired operation in the menu window 503, the selected operation is carried out.

Although Ward method is selected as a grouping algorithm in FIG. 5, the selection menu 501 can be pulled down to select other algorithm such as nearest neighbor method, furthest neighbor method, group average method, centroid method, median method, flexible method or the like. Similarity or dissimilarity is an index for indicating a degree of similarity between two expression patterns. Such index may be a distance where a shorter distance represents higher similarity, or a value such as a correlation coefficient where a higher value represents higher similarity. The former index is referred to as dissimilarity and the latter as similarity. Although Euclidean distance is selected as dissimilarity in FIG. 5, the selection menu 502 can be pulled down to select other types of (dis)similarity such as standardized squared Euclidean distance, Mahalanobis' general distance, Minkowsky distance or the like. The combination of grouping algorithm and dissimilarity type must be appropriate. For example, when centroid method, median method or flexible method is selected as the grouping algorithm, only squared Euclidean distance can be selected as dissimilarity.

FIG. 6 is a view showing an exemplary screen displayed upon selecting a command "display this subtree on a separate window" from the menu shown in FIG. 5. The selected subtree is rescaled and redisplayed according to the length from the root to the leaves. This display technique will allow the user to find more detailed state of the branches of the subtree. According to the present system, the selected subtree can be subjected to clustering again by selecting a grouping algorithm and/or (dis)similarity. For example, clusters distant from each other (such as clusters 401 and 402, and clusters 401 and 403 in FIG. 4) resulting from the first clustering can be selected and excluded to see a subtree of interest in more detail. A grouping algorithm and/or (dis)similarity can be selected from the grouping algorithm selection menu 501 and the (dis)similarity selection menu 502.

FIG. 7 is a view showing an exemplary screen displayed upon selecting a command "replace this subtree with icon" from the menu shown in FIG. 5. The subtree 505 can be replaced with an icon 701, by which a global state of the dendrogram can readily be observed. For example, gene groups with similar functions or gene groups with little expression observed can be assembled as a single icon.

FIG. 8 is a view showing an exemplary screen displayed upon selecting a command "search for keyword contained in this subtree" from the menu shown in FIG. 5. Among genes contained in the selected subtree, genes having gene information with a predetermined keywords are counted and the results are displayed as search results 801. When a keyword 802 is selected from the search results 801 with a mouse cursor 804 or the like, genes with this keyword 802 (in the figure, "ribosomal") are marked on the dendrogram with marks 803 or the like. By doing so, types of genes assembled in the subtree can readily be known. When the grouping is found to be failed, another grouping algorithm or (dis) similarity can be selected for another clustering. This would aid selection of more appropriate clustering method.

According to the present invention, an analysis can be made effectively on a produced dendrogram.

Thus, a method for displaying a dendrogram according to the present invention comprises the steps of: clustering a plurality of types of biopolymers based on a set of data obtained by experiments of the plurality of biopolymers under different conditions, and displaying the results thereof in a dendrogram format; selecting a subtree in the dendrogram; and displaying the selected subtree on a separate window.

The present invention may comprise the steps of: designating a different clustering method for the biopolymers included in the subtree displayed on the separate window; and clustering the biopolymers included in the subtree again according to the designated clustering method, and displaying the results thereof in a dendrogram format.

Furthermore, a method for displaying a dendrogram according to the present invention comprises the steps of: clustering a plurality of types of biopolymers based on a set of data obtained by experiments of the plurality of biopolymers under different conditions, and displaying the results thereof in a dendrogram format; selecting a subtree in the dendrogram; and replacing the selected subtree with an icon.

If necessary, the method may further comprise a step of restoring the subtree icon to the original dendrogram subtree format.

A method for displaying a dendrogram according to the present invention comprises the steps of: clustering a plurality of types of biopolymers based on a set of data obtained by experiments of the plurality of biopolymers under different conditions, and displaying the results thereof in a dendrogram format; selecting a subtree in the dendrogram; and from the biopolymers included in the selected subtree, counting and displaying the number of biopolymers containing in their biopolymer information a keyword from a keyword dictionary file.

A method for displaying a dendrogram according to the present invention comprises the steps of: clustering a plurality of types of biopolymers based on a set of data obtained by experiments of the plurality of biopolymers under different conditions, and displaying the results thereof in a dendrogram format; selecting a subtree in the dendrogram; designating a keyword; and displaying a location of a biopolymer in the dendrogram, which includes the designated keyword in its biopolymer information.

According to the above-described methods, the biopolymers may be cDNAs, RNAs, DNA fragments or genes.

A system for displaying a dendrogram according to the present invention comprises: a clustering processor for clustering a plurality of types of biopolymers based on a set of data obtained by experiments of the plurality of biopolymers under different conditions, and analyzing the results thereof to display them in a dendrogram format; a display section for displaying the dendrogram; input means; and a keyword dictionary file for storing keywords of biopolymer information. The input means may be a keyboard or a mouse which is used for selecting a branch in the dendrogram, selecting a clustering method and the like. The keyword dictionary file may be used to evaluate whether the results of clustering have turned out to be successful.

This system for displaying a dendrogram may have a function of displaying a subtree selected by the input means on a separate window. Alternatively, the system may have a function of designating a different clustering method for the subtree displayed on the separate window to cluster the biopolymers included in the subtree again according to the designated clustering method, and displaying the results thereof in a dendrogram format.

The system for displaying a dendrogram may have a function of replacing the subtree selected by the input means with an icon, and a function of restoring the subtree icon to the original subtree in the dendrogram format.

The system for displaying a dendrogram may have a function of counting and displaying the number of biopolymers containing in their biopolymer information a keyword from a keyword dictionary file, and/or a function of displaying a location of a biopolymer in the dendrogram, which includes the designated keyword.

According to the system for displaying a dendrogram of the invention, the biopolymers may be DNAs, RNAs, DNA fragments or genes.

BRIEF DESCRIPTION OF THE DRAWINGS

FIG. 11 is a diagram showing an exemplary gene information structure.

FIG. 12 is a diagram showing an exemplary cluster structure.

DESCRIPTION OF THE PREFERRED EMBODIMENTS

Hereinafter, the present invention will be described by way of examples with reference to the accompanying drawings. Although genes are exemplified as a subject of clustering in the following examples, the present invention is not limited thereto and is also applicable to other general biopolymers such as cDNAs, RNAs and DNA fragments.

Figure 1:
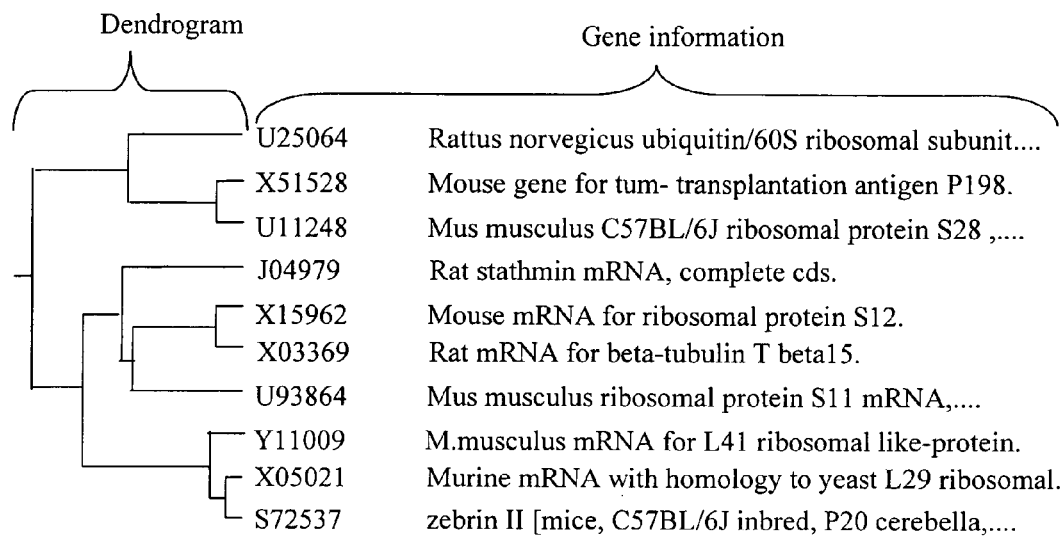
FIG. 1 is a diagram showing an exemplary display of results of a standard clustering analysis.
Figure 2:
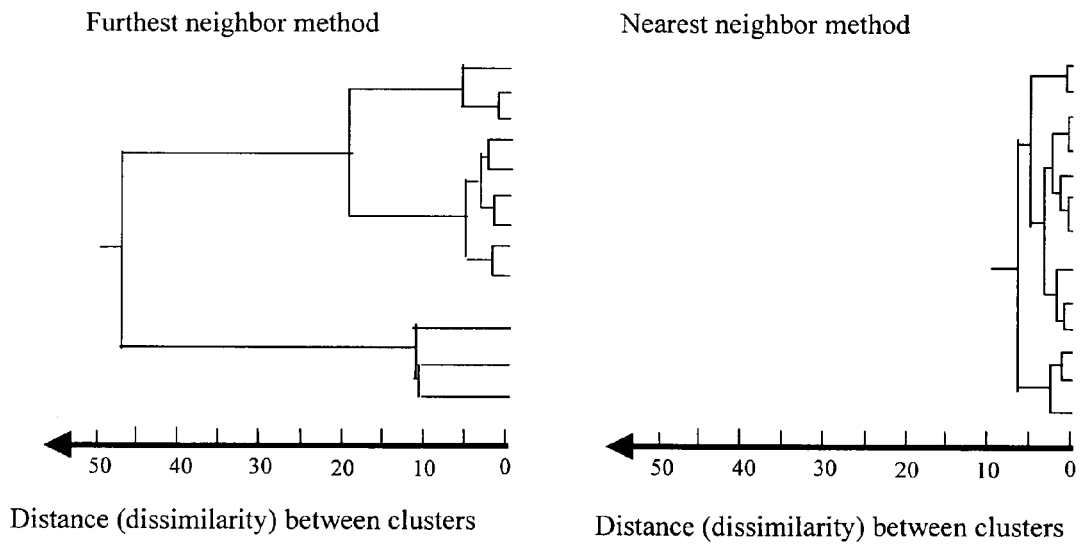
FIG. 2 is a diagram showing an example of difference between clustering methods.
Figure 3:
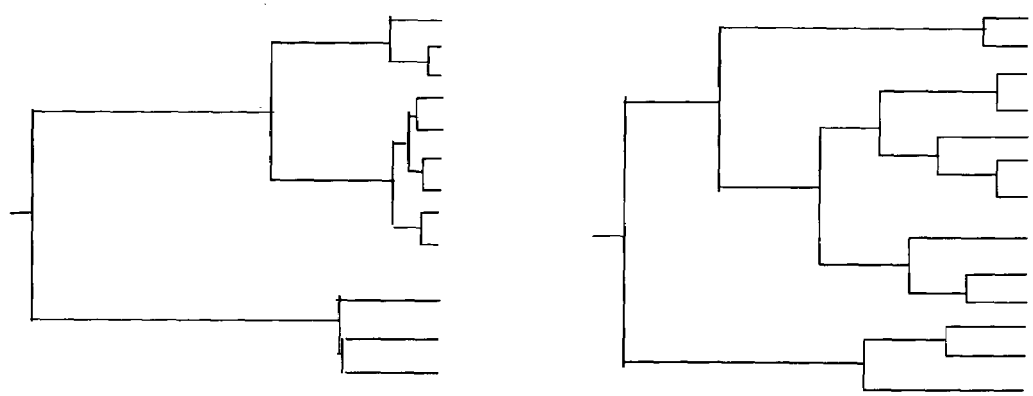
FIG. 3 is a diagram showing exemplary dendrograms with normalized distance (dissimilarity) obtained by different clustering methods.
Figure 4:
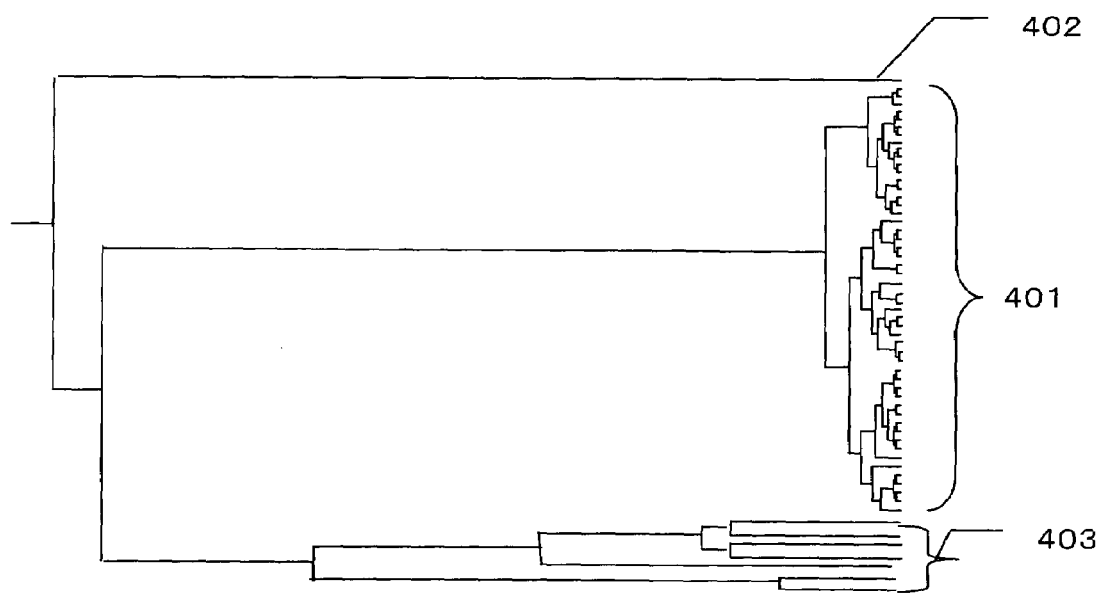
FIG. 4 is a diagram showing an exemplary dendrogram including a gene group with similar expression patterns.
Figure 5:
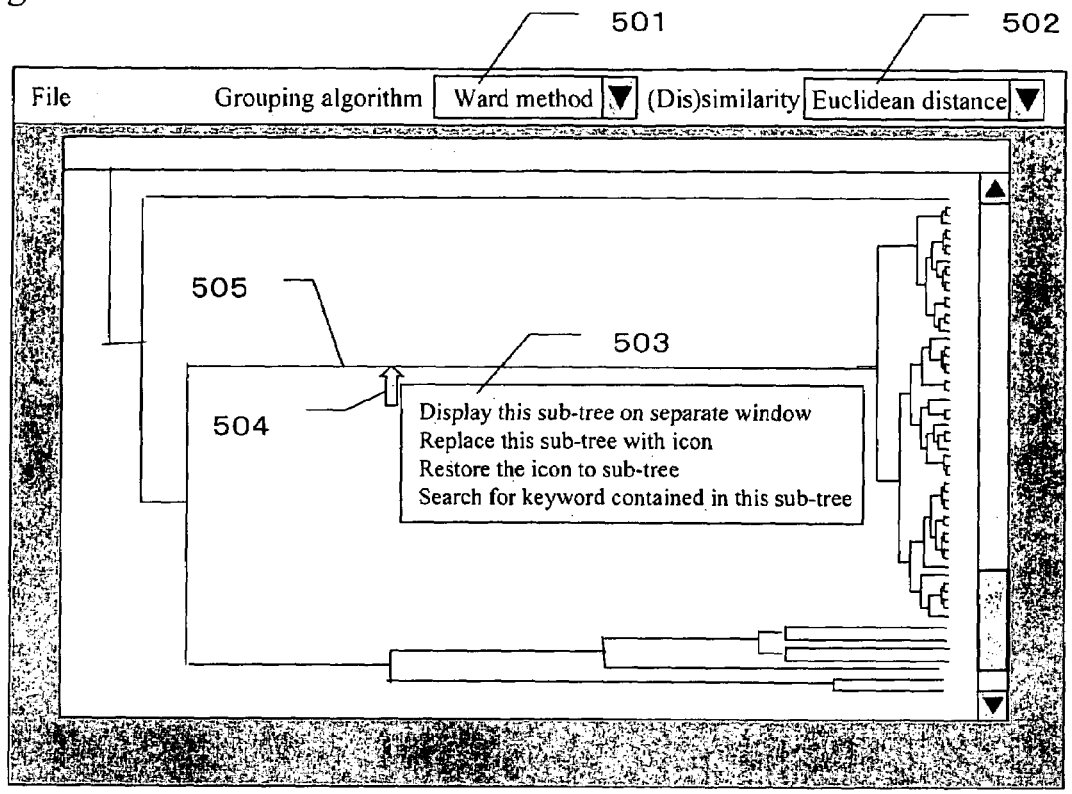
FIG. 5 is a view showing an exemplary display screen according to a dendrogram displaying system of the invention.
Figure 6:
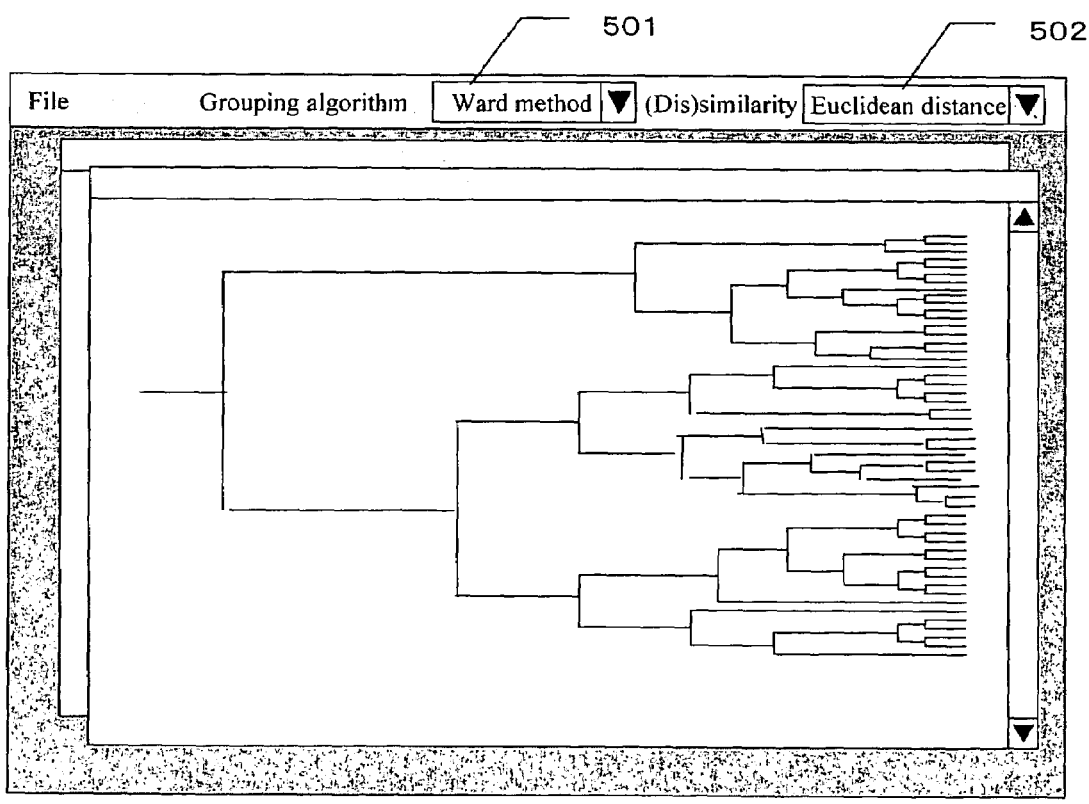
FIG. 6 is a view showing another exemplary display screen according to a dendrogram displaying system of the invention.
Figure 7:
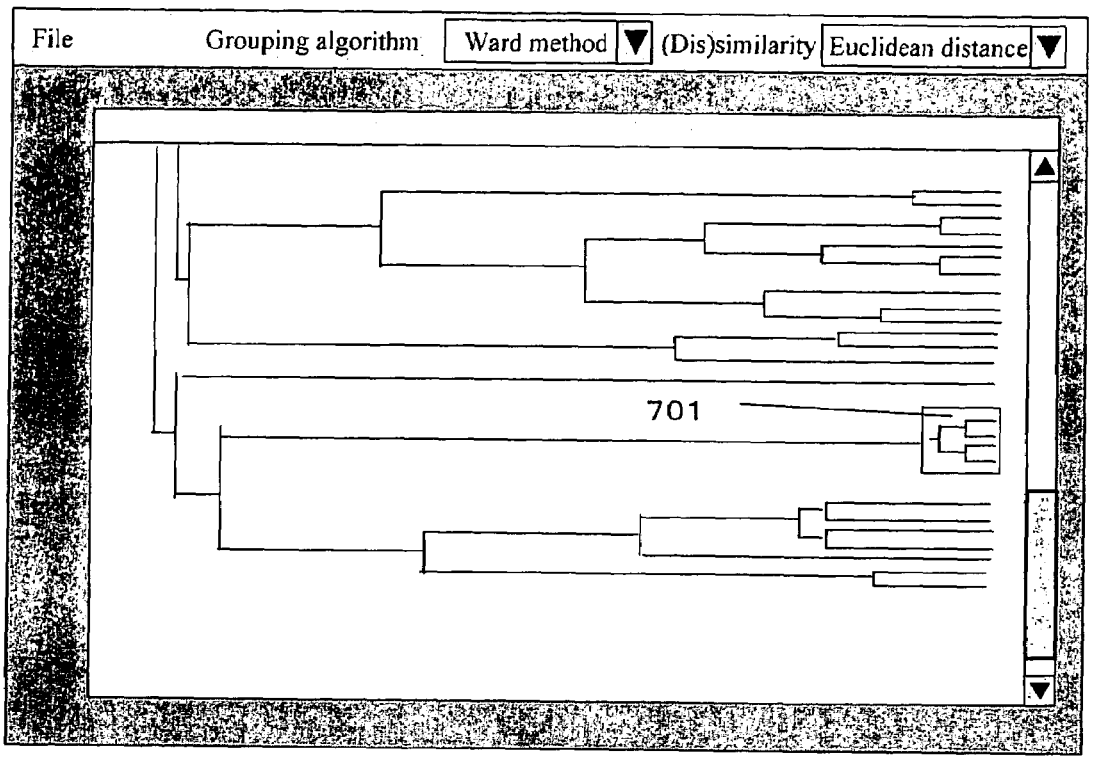
FIG. 7 is a view showing yet another exemplary display screen according to a dendrogram displaying system of the invention.
Figure 8:
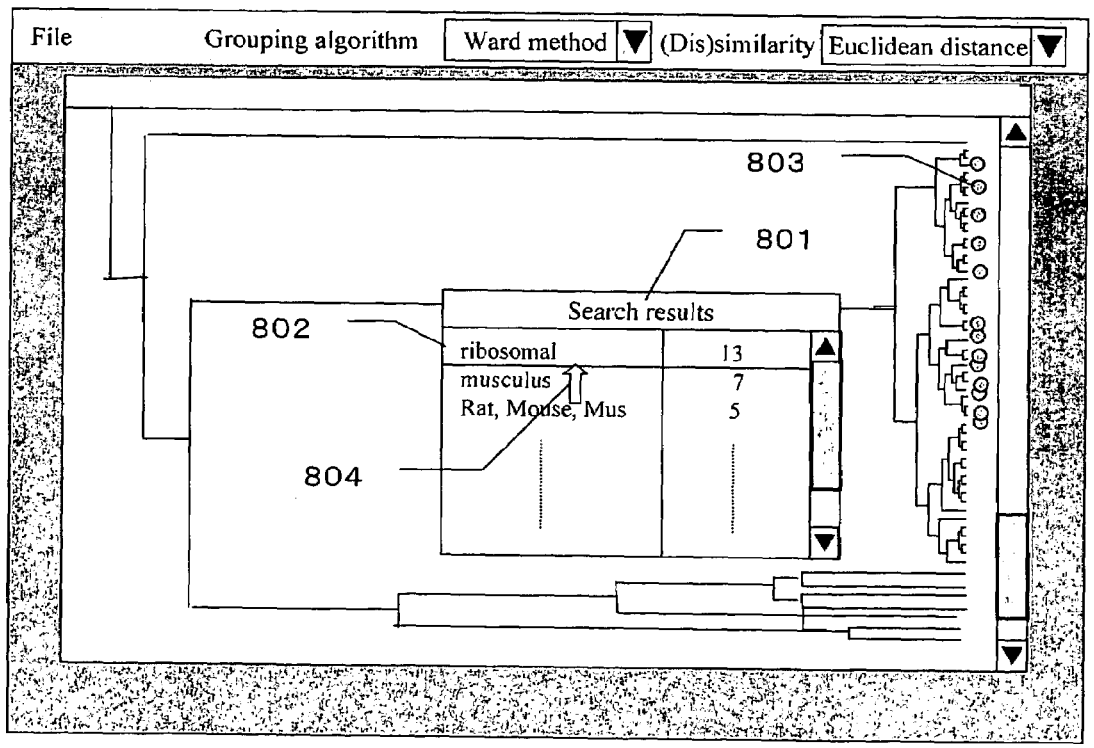
FIG. 8 is a view showing still yet another exemplary display screen according to a dendrogram displaying system of the invention.
Figures 9, 10:
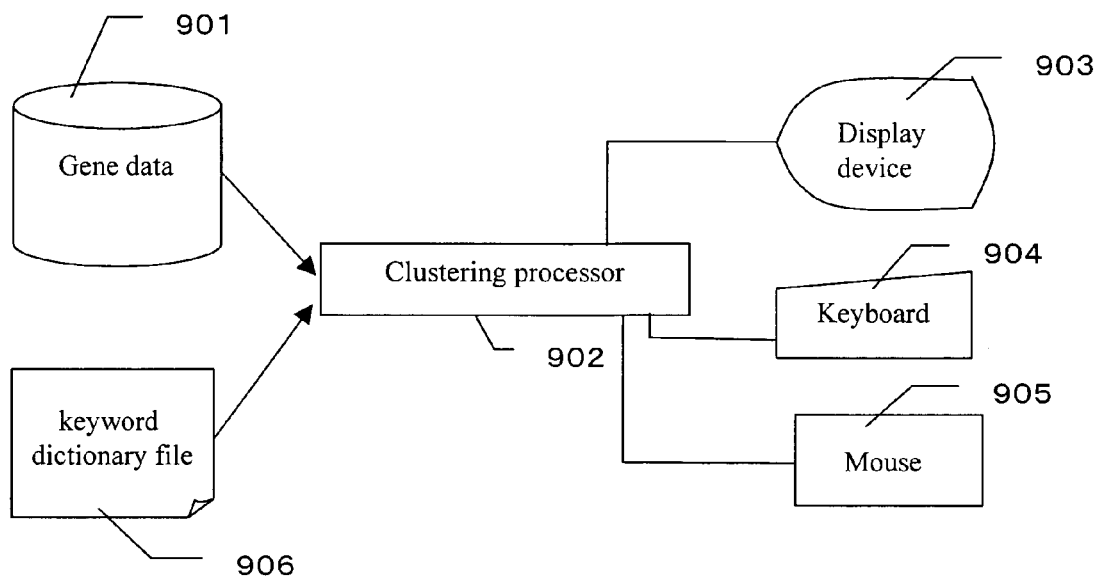
FIG. 9 is a schematic view showing an exemplary configuration of a dendrogram displaying system of the invention.
FIG. 10 is a diagram showing exemplary gene expression pattern data.

FIG. 9 is a schematic view showing a configuration of an exemplary system for displaying a dendrogram according to the invention. The system is provided with gene data 901 for storing gene information and gene expression patterns, a clustering processor 902 for clustering based on the gene expression patterns, and analyzing and displaying the results in a dendrogram format, a display device 903 on which the dendrogram is displayed, input means such as a keyboard 904 and a mouse 905 for selecting a branch in the dendrogram or for selecting a clustering method, and a keyword dictionary file 906 for storing keywords of gene information to provide means for evaluating whether the results of clustering are in a user's desired form. The clustering processor 902 is realized with a computer and a program thereof. In stead of the storage medium 901, gene data can be acquired from a database managed by a remote server computer communicating with the system via a network or the like.

FIG. 10 is a schematic view showing a specific structure of gene expression pattern data stored in the gene data 901. According to the present algorithm, the data is stored as a two-dimensional array. Specifically, numerated data of an expression level (brightness of hybridized fluorescent signal) of a gene corresponding to gene ID (id) under an experiment case (no) is stored as Exp[id][no]. The results obtained from a DNA chip spotted with m numbers of genes at different positions correspond to a single experiment case.

FIG. 11 is a diagram showing an example of a gene information structure for storing information of a gene stored in the gene data 901. The gene structure includes members representing gene ID (1101), ORF of the gene (1102), name of the gene (1103) and a function of the gene (1104). The example shown in FIG. 11 is merely an example, and the gene information structure may include information other than the attributes mentioned in the figure.

FIG. 12 is a diagram showing exemplary structures indicating clusters used in the clustering. Each cluster structure corresponds to either a node or a leaf in a dendrogram. Each of the cluster structures is managed in a window unit. Nodes or leaves in the same window are provided with the same window ID (1207). In order to identify nodes or leaves in the same window from each other, each cluster structure is uniquely assigned with a clusterNo (1205). There are three types of cluster structures, and the values of type (1201) may be leaf, node or icon.

A leaf-type cluster structure corresponds to a single gene ID (1206), i.e., a single gene. Based on the gene ID, data of the gene information structure can be referred. A node-type cluster structure is generated upon every joining step during the clustering. Based on this node-type cluster, the two clusters that have been joined can be referred to as left value (1202) and right value (1203), and the distance ((dis)similarity) therebetween is stored as distance value (1204). The left and right values are represented by clusterNo (1205). An icon-type cluster structure is generated upon replacing the subtree with an icon to be treated in the same manner as the leaves upon display. An icon indicating the subtree is provided on the tip of the branch. An actual cluster at the root of the subtree can be referred to from the left value (1202).

Figure 13:
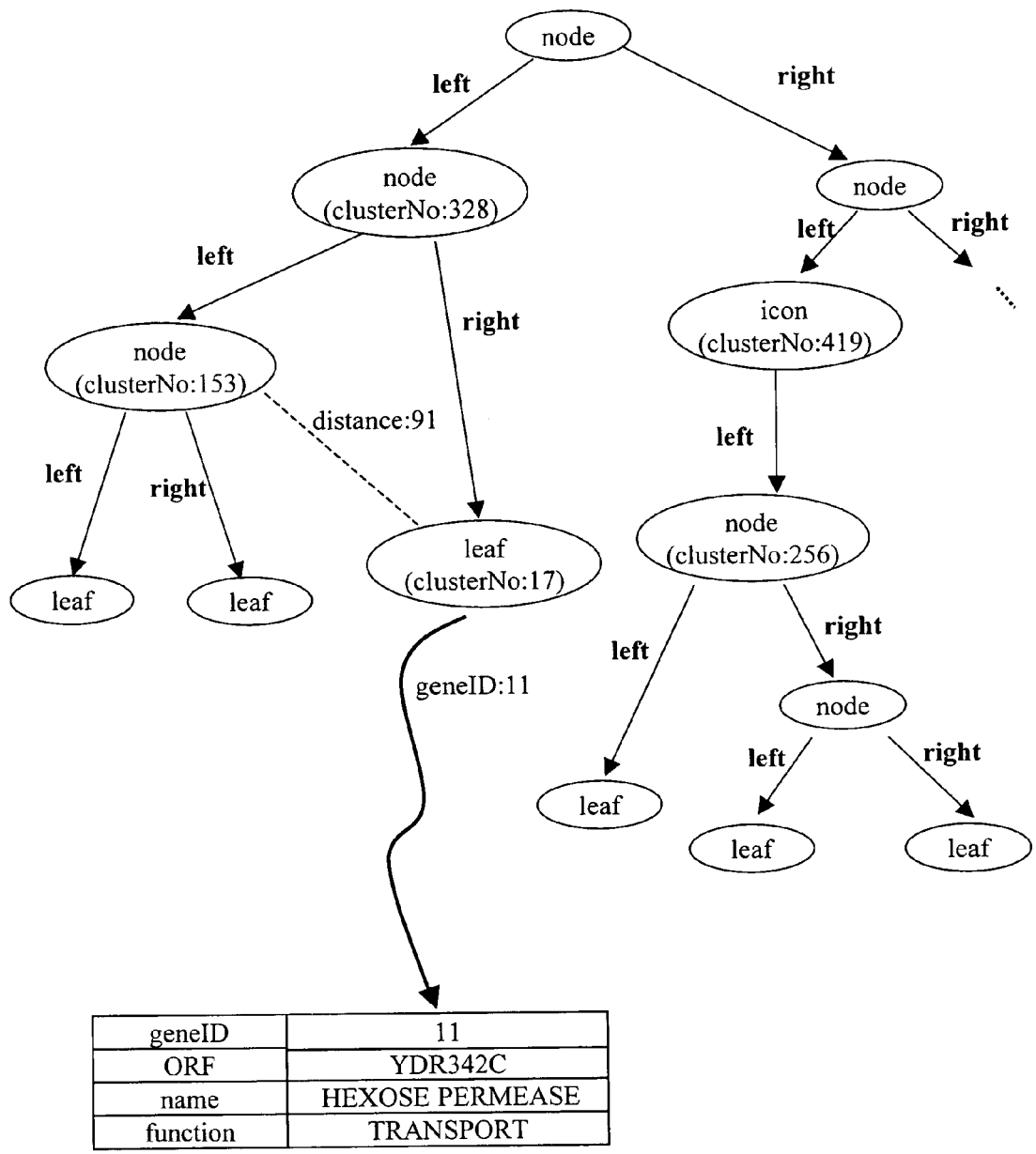
FIG. 13 is a diagram showing an example for generating a cluster tree structure.

FIG. 13 is a diagram showing a data structure of the cluster structures exemplified in FIG. 12. The data structure is generated during the course of the clustering analysis. First, the cluster structures start with only leaf-type structures. Then, as clustering takes place, every two cluster structures are joined together upon which a node-type cluster structure is generated, thereby forming a tree structure. Each node-type cluster structure includes information of clusterNo of the two joined child nodes and the distance ((dis)similarity) therebetween. Relative gene information can be referred to based on gene ID registered in the leaf-type cluster structures. If a subtree is replaced with an icon, an icon-type cluster is inserted into the tree to be treated as a leaf (clusters downstream from the icon-type cluster are not displayed). For restoring the icon, clusters upstream and downstream from the icon-type cluster are rejoined).

Figure 14:
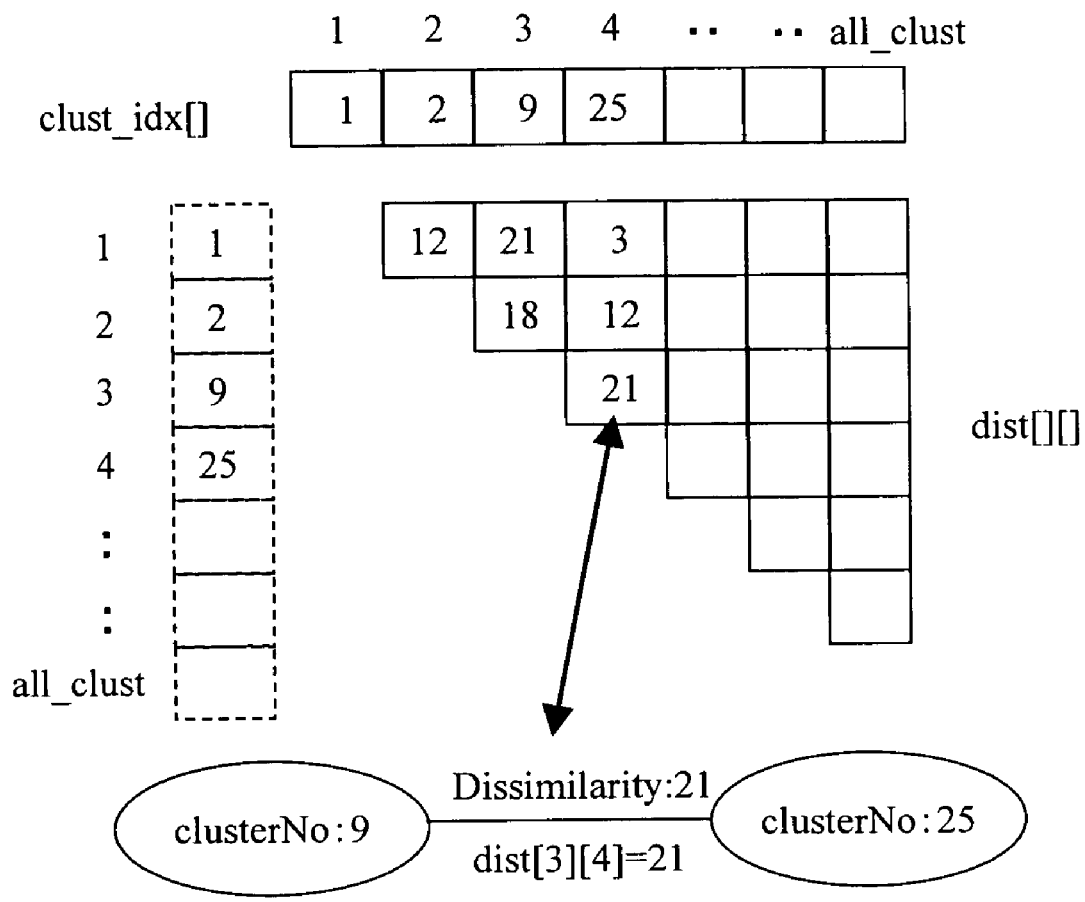
FIG. 14 is a diagram showing an exemplary array for storing distances between clusters.

FIG. 14 is a diagram showing an example of an array for storing dissimilarity values (i.e., distances between clusters) during the course of the clustering analysis. As shown in the figure, dissimilarity values are stored as a two-dimensional array dist[ ][ ]. clusterNo(1205) of clusters corresponding to the indices of the two-dimensional array dist[ ][ ] are stored in clust_idx[ ]. Specifically, the value of the dissimilarity dist[i][j] indicates a dissimilarity value between clusters whose clusterNo are clust_idx[i] and clust_idx[j]. For example, as can be appreciated from FIG. 14, the value of dissimilarity dist[3][4] between clusterNo: 9 as clust_idx[3] and clusterNo: 25 as clust_idx[4] is 21.

Figure 15:
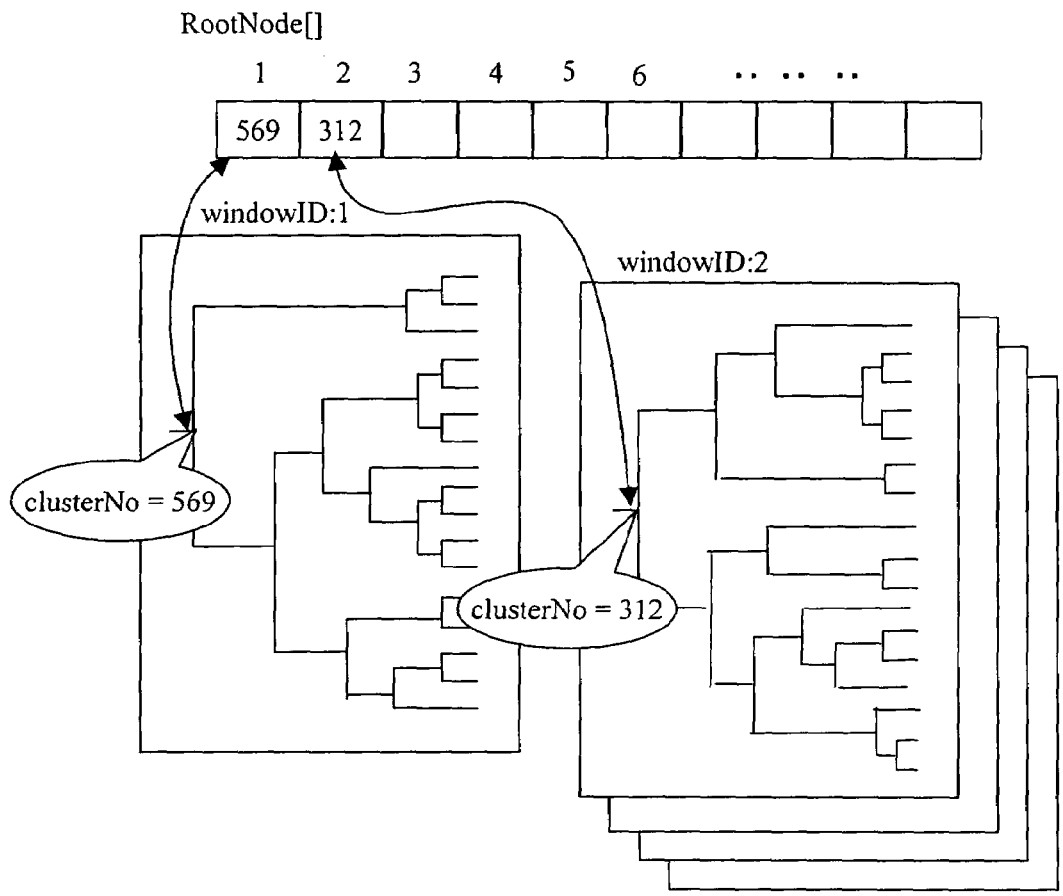
FIG. 15 is a diagram showing an exemplary array for storing root nodes of respective windows.

FIG. 15 is a diagram showing an example of an array for storing root nodes of respective windows. Specifically, the clusterNo of the cluster at the root node in each display window is stored in an array RootNode[ ]. In the example shown in FIG. 15, the value of RootNode[1] is 569, which means that the root node of the dendrogram displayed on a display window corresponding to window ID: 1 is a cluster of clusterNo: 569. Similarly, since the value of RootNode[2] is 312, the root node of the dendrogram displayed on a display window corresponding to window ID: 2 is a cluster of clusterNo: 312.

Figure 16:
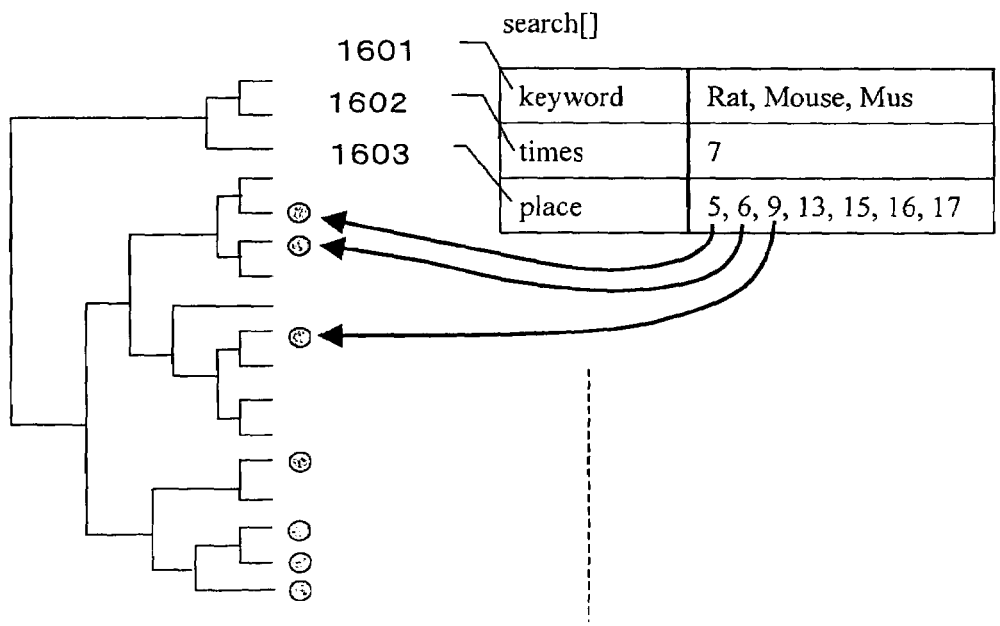
FIG. 16 is a diagram showing an example of a structure for storing a query of search and its results.

FIG. 16 is a diagram showing an example of a search structure for storing a query of search and its results. For each keyword registered in the keyword dictionary file 906, a single structure is generated. When some of synonyms are included in the keywords, they can be processed as a single search target. The search structure includes members such as keyword (1601) for registering a keyword as a search target, times (1602) indicating the number of the keyword contained in the subtree, place (1603) for storing locations of genes on the dendrogram whose gene information include the keyword. As illustrated in FIG. 16, synonyms such as Rat, Mouse and Mus can collectively be registered in the keyword member so that these three keywords can be treated as an identical search target.

Figure 17:
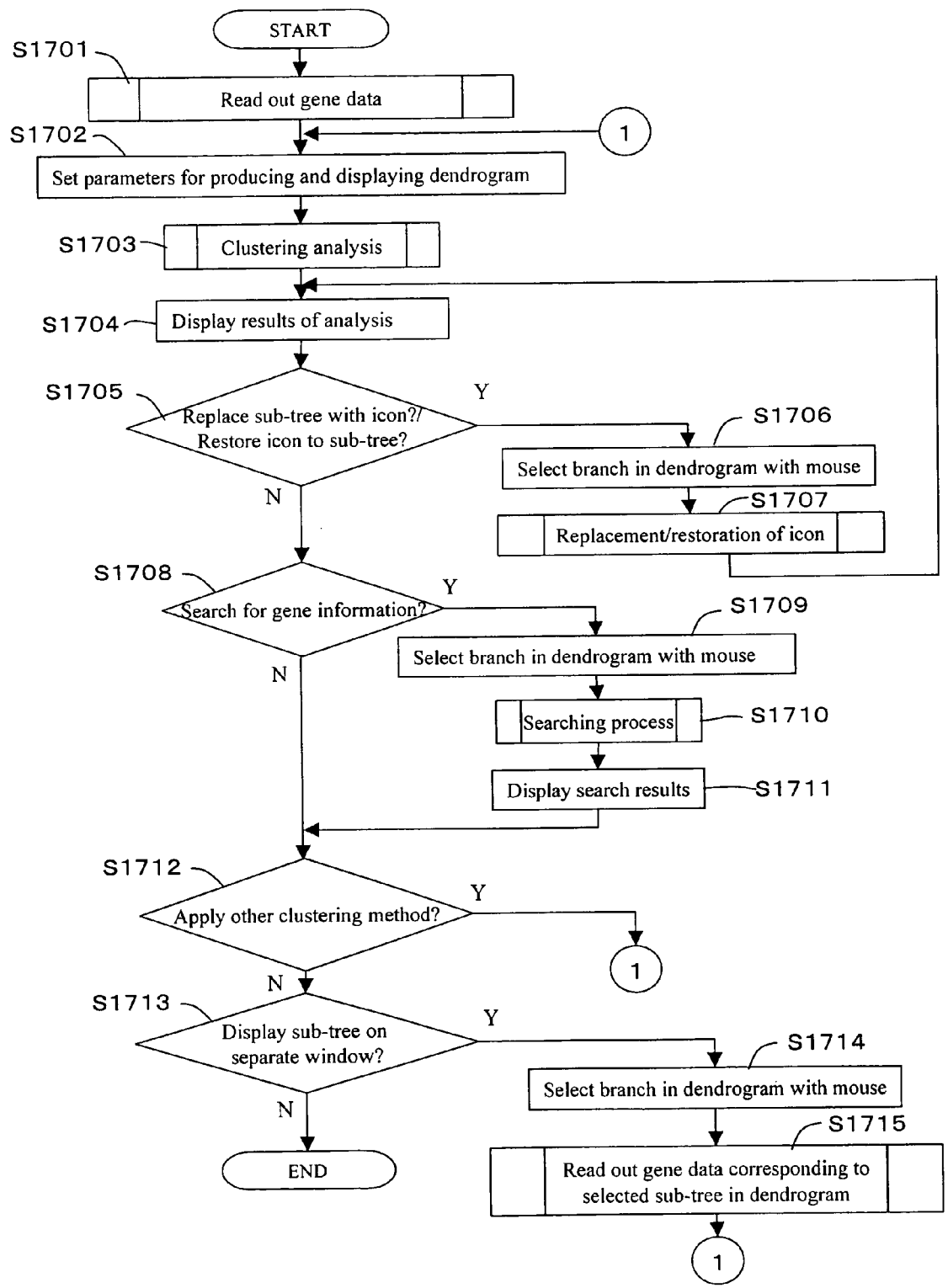
FIG. 17 is a flowchart showing a general process of the present system.

FIG. 17 is a flowchart of a general process of the present system.

First, data is read out from the gene data 901 to the clustering processor 902 (Step 1701), which will be described later in more detail. Then, various parameters required for carrying out a clustering analysis and displaying results are set (Step 1702). In the present example, a grouping algorithm, a type of (dis)similarity, and whether or not gene information should be displayed are determined.

Next, a clustering analysis takes place (Step 1703), and the results thereof are displayed (Step 1704). Detail of the clustering analysis will be described later. During this clustering analysis, information necessary for displaying a dendrogram is collected and input into cluster structures. The results of the analysis are displayed based on these cluster structures and the information of RootNode[ ] indicating the clusterNo of the root nodes on respective window. When the cluster structure is of an icon-type, it is processed as a leaf, and an icon representing a subtree is provided at the tip of the branch.

When the subtree in the displayed dendrogram should be simplified as an icon, or when the icon is to be restored to the original subtree, the following process is conducted (Step 1705). A branch in the dendrogram is selected with a mouse (Step 1706), and the corresponding subtree is replaced with the icon or an icon is restored to a subtree (Step 1707). Replacement and restoration processes will be described later in detail. Thereafter, the results of the analysis are displayed again (Step 1704).

When search should be conducted in the displayed dendrogram based on a keyword stored in the keyword dictionary file 906, the following process is carried out (Step 1708). A branch in the dendrogram is selected with a mouse (Step 1709), and search is performed (Step 1710). The detail of the search will be described later. Since information required for display will be stored in search structures by searching process 1710, a search results window is newly generated based on the search structures to display the results (Step 1711). By selecting a keyword in the search results window with a mouse or the like, the location(s) of the keyword on the dendrogram is(are) marked based on the information of the place member(s) of the search structures.

When clustering based on another combining algorithm or (dis)similarity type should be conducted to the displayed dendrogram, the process returns to Step 1702 (Step 1712). Examples of cluster-combining algorithm include nearest neighbor method, furthest neighbor method, group average method, centroid method, median method, Ward method and flexible method. According to the nearest neighbor method, the furthest neighbor method, the group average method, the Ward method and the flexible method, dissimilarity simply becomes larger as clusters are merged. As two clusters are merged into one, the merged cluster may become closer to or farther from other clusters. The former is referred to as space contraction, and the latter is referred to as space expansion. A case where the distance is unchanged is referred to as space preservation. The nearest neighbor method has a characteristic of space contraction, and the furthest neighbor method and Ward method each have a characteristic of space expansion. The group average method, the centroid method and the median method each have a characteristic of space preservation. The flexible method may have any of the space characteristics depending on parameter settings. There are various types of (dis) similarity. Typical examples of dissimilarity include squared Euclidean distance, standardized squared Euclidean distance, Mahalanobis' general distance and Minkowsky distance. An appropriate dissimilarity can be selected among the above-mentioned distances considering the above-described characteristic and the like.

When a subtree in the displayed dendrogram should be displayed on a separate window (Step 1713), a branch to be displayed on the separate window is selected in the dendrogram with a mouse (Step 1714). Then, data corresponding to the selected subtree in the dendrogram is read out (Step 1715), and the process returns to Step 1702. Process of reading out data corresponding to the selected subtree will be described later in detail. When no further selection is to be made, the whole process is ended.

Figure 18:
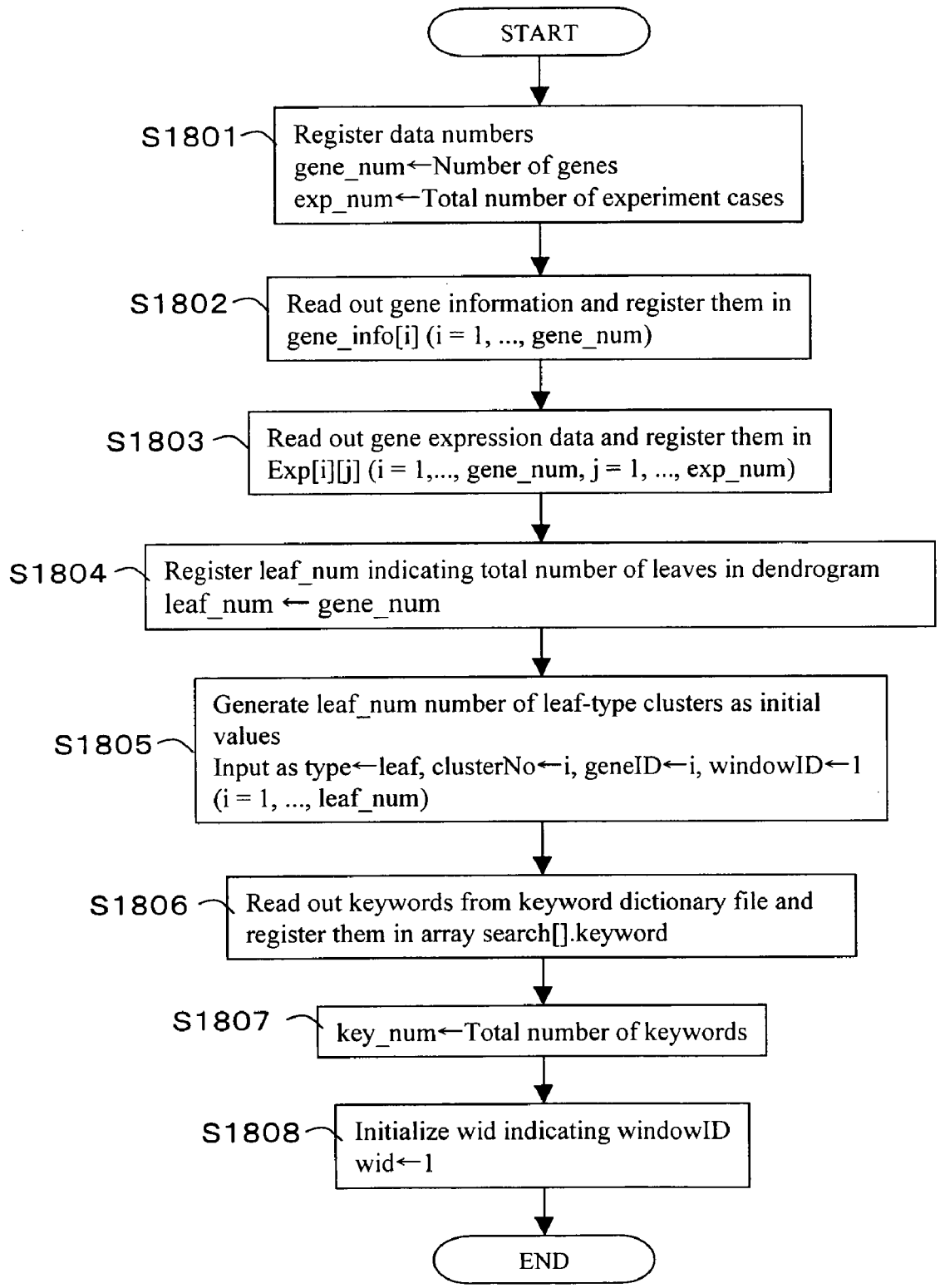
FIG. 18 is a flowchart showing a process of reading out gene data.

FIG. 18 is a detailed flowchart of the reading out process 1701 in FIG. 17.

First, the total numbers of genes and experiment cases are registered in gene_num and exp_num, respectively (Step 1801). Then, gene information is read out from the gene data 901 to be registered in gene information structures gene_info[i] (where i=1, . . . , gene_num) (Step 1802). Gene expression data is read out from the gene data 901 to be registered in Exp[i][j] (where i=1, . . . , gene_num, and j=1, . . . , exp_nun) (Step 1803). Then, gene_num is input into leaf_num indicating the total number of leaves in the dendrogram (Step 1804).

Next, leaf-type cluster structures are generated as initial values. The leaf_num number of cluster structures are generated. And for i=1, . . . , leaf_num, type member, clusterNo, geneID and windowID are set to leaf, i, i and 1 respectively (Step 1805). Then, keywords stored in the keyword dictionary file 906 are read out. For each keyword, a search structure is generated, and the keyword is registered as search[ ].keyword (Step 1806). The total number of keywords is substituted for key_num (Step 1807). wid representing window ID is set to 1 (Step 1808), and the process is ended.

Figure 19:
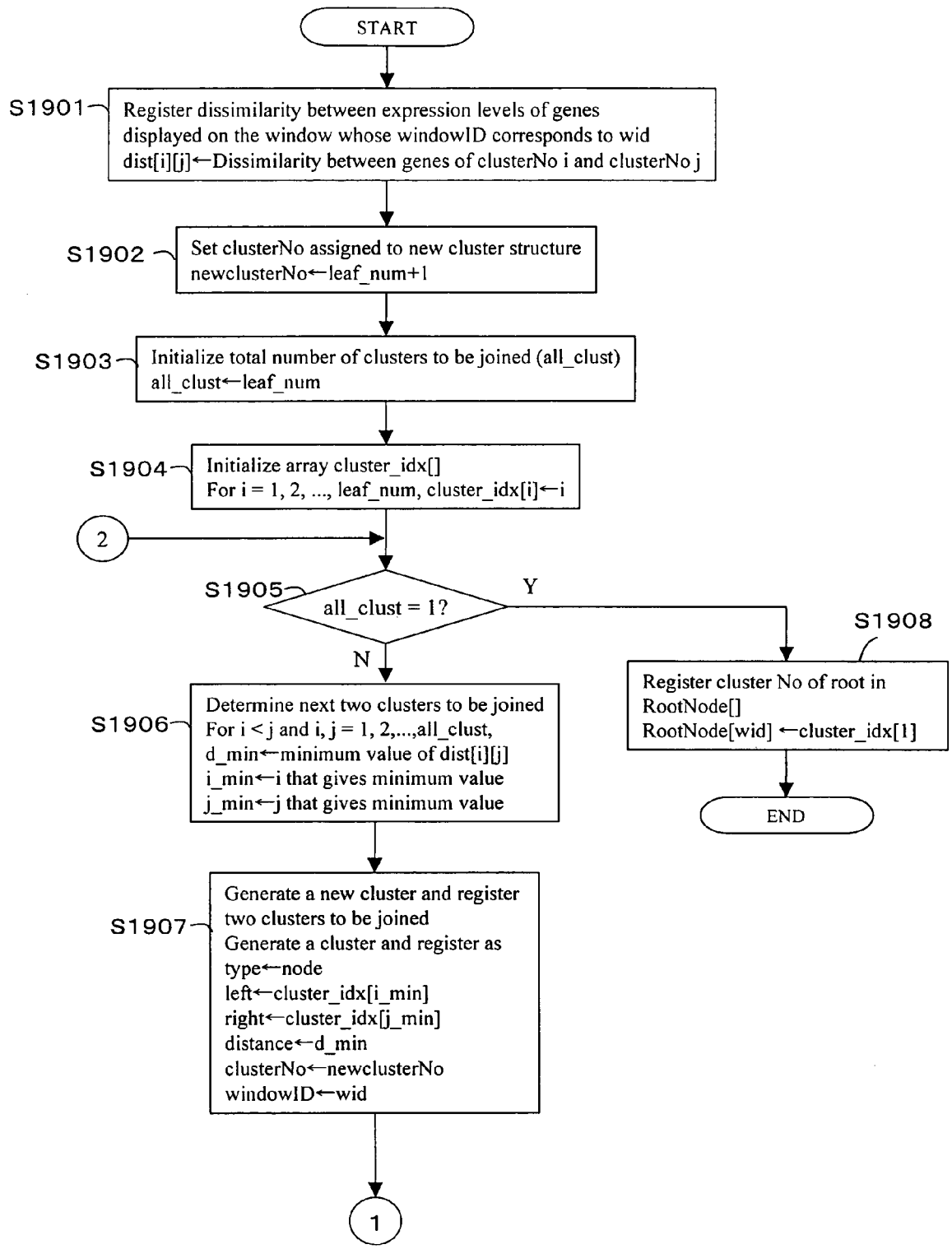
FIG. 19 is a flowchart showing a process for clustering analysis.
Figure 20:
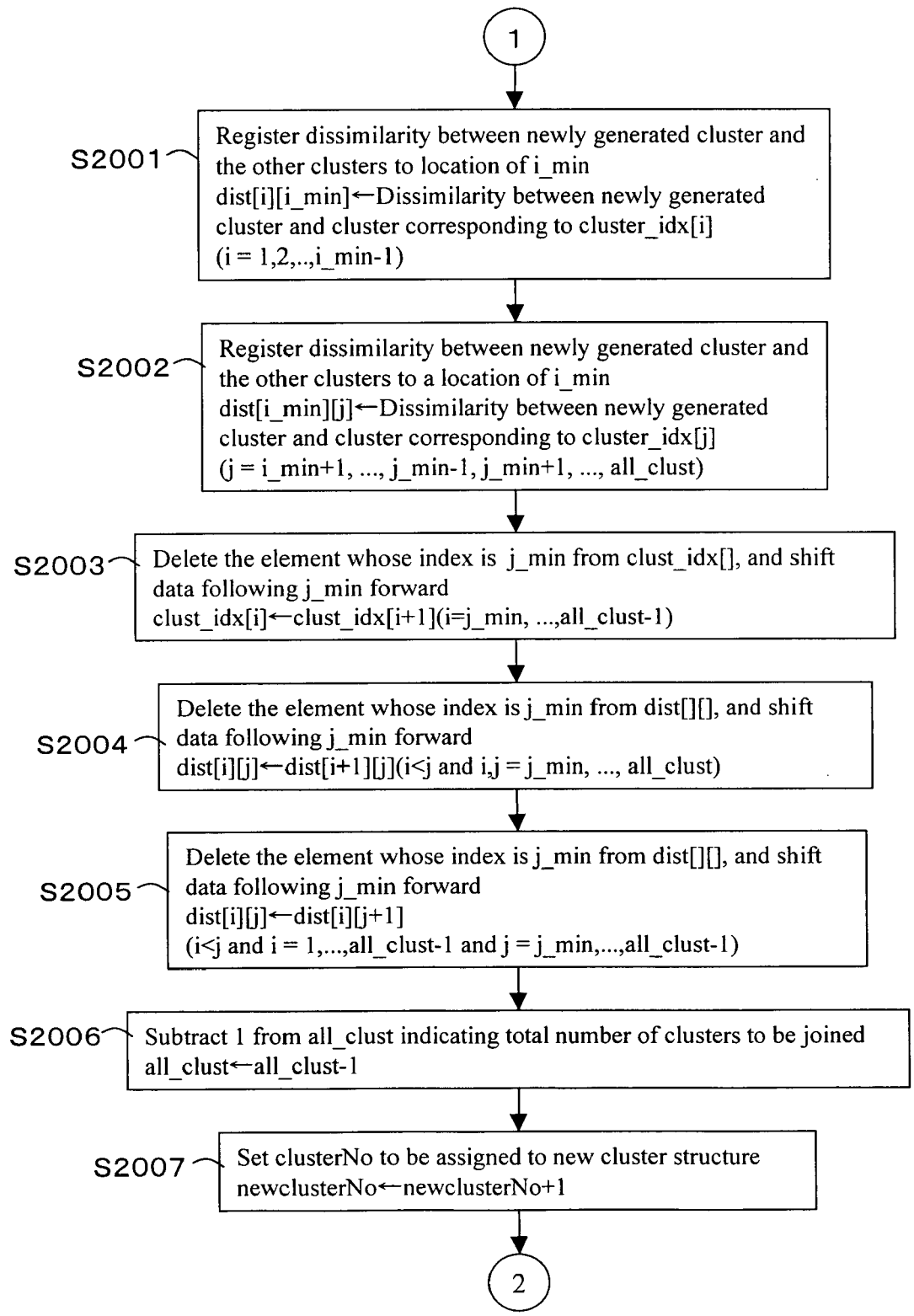
FIG. 20 is another flowchart showing a process for clustering analysis.

FIGS. 19 and 20 are detailed flowcharts of clustering analysis process 1703 in FIG. 17.

Dissimilarity between expression levels of genes displayed on the window whose window ID corresponds to wid is calculated. Dissimilarity between genes of clusterNo i and clusterNo j is registered as dist[i][j] (Step 1901). According to the present algorithm, clusterNo is sequentially assigned every time a cluster is generated starting from 1. Accordingly, for a next cluster to be generated, leaf_num+1 is substituted for newclusterNo as the number of the next cluster (Step 1902). As array information for storing distances (dissimilarity) between clusters, leaf_num is substituted for all_clust representing the number of clusters to be joined, and for i=1, . . . , leaf_num, i is substituted for cluster_idx[i] for initialization. The number of the clusters to be joined (all_clust) is evaluated as to whether or not it equals to 1. When it does not equal to 1, the following processes are repeated until it equals to 1 (Step 1905).

First, based on the previously determined distance (dissimilarity) between clusters, clusters to be joined next are determined. For i<j and i, j=1, 2, . . . , all_clust, a minimum value of dist[i][j], and i and j that give the minimum value are obtained to substitute for d_min, i_min and j_min, respectively. Clusters to be joined next are clusters of clusterNo represented by cluster_idx[i_min] and cluster_idx[j_min]. A cluster is newly generated, and type, left, right, distance, clusterNo and windowID are set to node, cluster_idx[i_min], cluster_idx[j_min], d_min, newclusterNo and wid, respectively (Step 1907). Which one of the clusters should be assigned as left member and the other as right member may be determined by providing a predetermined criterion such as comparison of expression levels.

Then, information of the array storing distances between clusters is updated. First, a distance ((dis)similarity) between a newly generated-cluster and other cluster is calculated and overwritten on a location of array dist[ ][ ] where a distance between a cluster corresponding to i_min and other cluster is stored. For i=1, 2, . . . , i_min −1, dissimilarity between the newly generated cluster and a cluster whose clusterNo corresponds to cluster_idx[i] is registered in dist[i][i_min] (Step 2001). For j=i_min+1, . . . , J_min−1, j_min+1, . . . , all_clust, dissimilarity between the newly generated cluster and a cluster corresponding to cluster_idx[j] is registered as dist[i_min][j] (Step 2002).

Next, information relative to j_min is deleted and all of the array data following j_min is shifted forward. For i=j_min, . . . , all_clust−1, clust_idx[i+1] is substituted for clust_idx[i] (Step 2003). Then, for i and j that satisfy i<j and i, j=j_min, . . . , all_clust, dist[i+1][j] is substituted for dist[i][j] (Step 2004). Thereafter, for i and j that satisfy i<j, i=1, . . . , all_clust-1 and j=j_min, . . . , all_clust_1, dist[i][j+1] is substituted for dist[i][j] (Step 2005).

Finally, 1 is subtracted from all_clust indicating the number of clusters to be joined (Step 2006). NewclusterNo indicating clusterNo assigned to a new cluster structure is added with 1 (Step 2007).

The above-described process is repeated until all_clust becomes 1. When all_clust becomes 1, cluster_idx[1] indicating clusterNo of a root node of the present window is substituted for RootNode[wid] (Step 1908) and the process is ended.

Figure 21:
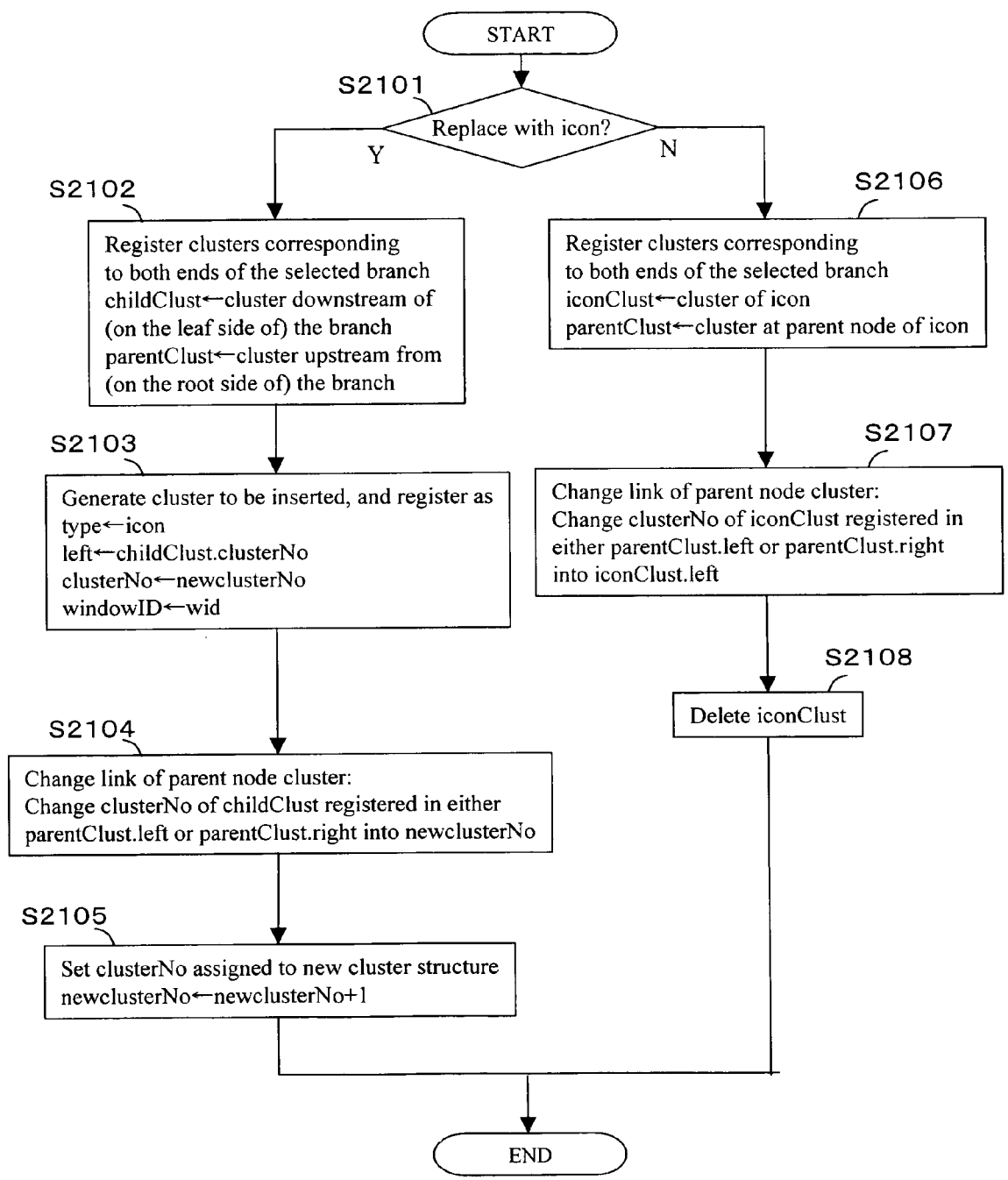
FIG. 21 is a flowchart showing a process for replacement/restoration of icon.

FIG. 21 is a detailed flowchart of process 1707 in FIG. 17 for replacement and restoration of an icon.

Clusters corresponding to both ends of the branch selected at Step 1706 are registered. The downstream (leaf side) cluster is substituted for childClust and the upstream (root side) cluster is substituted for parentClust (Steps 2101 and 2102). Then, a new icon-type cluster is generated and inserted between the childClust and parentClust. Specifically, a cluster is generated, where type, left, clusterNo and windowID are set to icon, childClust.clusterNo, newclusterNo and wid, respectively (Step 2103). To re-link the pointer, clusterNo of childClust registered in either parentClust.left or parentClust.right is replaced with newclusterNo (Step 2104). As the total number of clusters will be increased by one, newclusterNo is added with 1 to indicate clusterNo assigned to a new cluster structure (Step 2105). Then, the process is ended.

When restoration of the subtree icon is selected from the menu, first, clusters corresponding to both ends of the branch selected at Step 1706 in FIG. 17 are registered. The cluster of the icon downstream from (on the leaf side of) the branch selected at Step 1706 and the cluster at the parent node of the icon are substituted for iconClust and parentClust, respectively (Steps 2101 and 2106). The pointer linking the cluster of the icon is re-linked to the clusters of the subtree, and the cluster of the icon is deleted. Specifically, clusterNo of iconClust registered in either parentClust.left or parentClust.right is changed into iconClust.left (Step 2107). Then, iconClust is deleted (Step 2108) and the process is ended.

Figure 22:
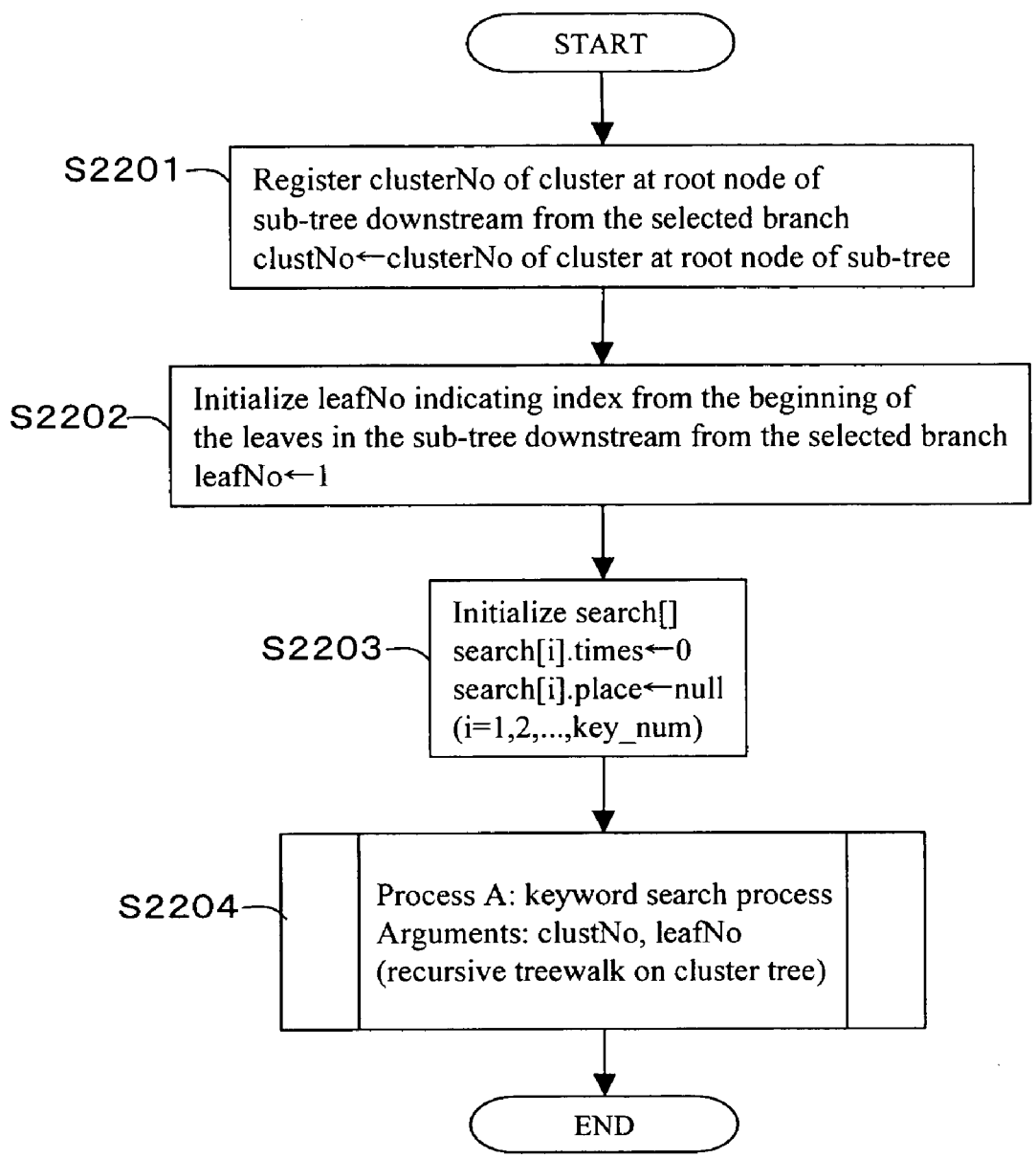
FIG. 22 is a flowchart showing a process of searching in gene information

FIG. 22 is a detailed flowchart of searching process 1710 in FIG. 17.

First, clusterNo of a cluster at a root node of a subtree downstream from the selected branch is substituted for clustNo (Step 2201). Then, leafNo indicating an index assigned from the beginning of the leaves in the subtree is initialized to 1 (Step 2202). For i=1, . . . , key_num, search[i].times and search[i].place are initialized to 0 and null, respectively (Step 2203). Then, treewalk is recursively performed on the cluster tree to search for a gene having the keyword designated in search (Process A) (Step 2205). Here, clustNo and leafNo are given as arguments. The detail of keyword searching process will be described later in detail. After Process A, the search results are input into the search structure and the process is ended.

Figure 23:
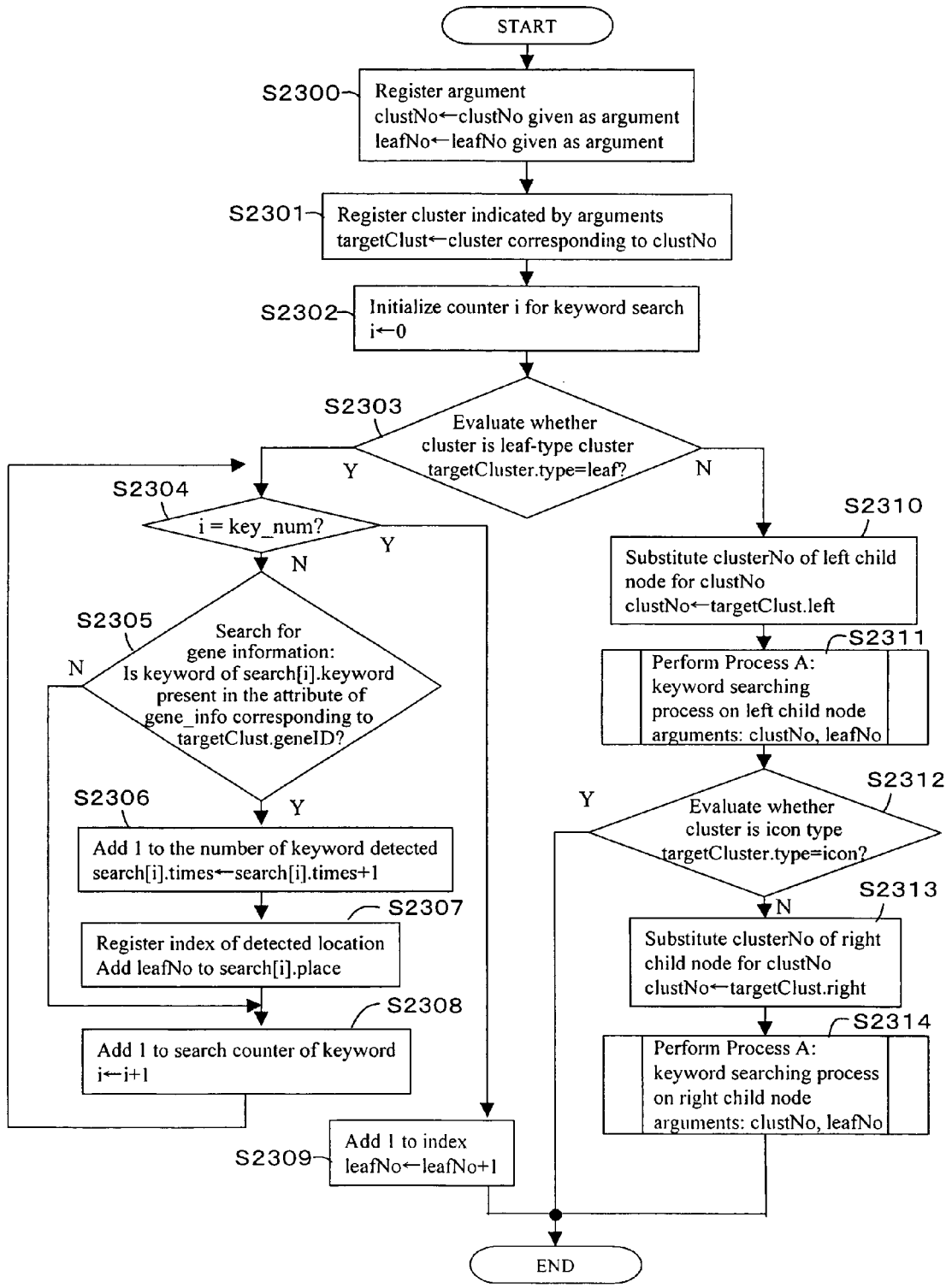
FIG. 23 is a flowchart showing a process of searching for a keyword (Process A).

FIG. 23 is a detailed flowchart of keyword searching process (Process A) in FIG. 22.

The given arguments clustNo and leafNo are substituted for clustNo and leafNo, respectively (Step 2300). The cluster corresponding to clusterNo is substituted for targetClust (Step 2301). A counter i for keyword search is set to 0 (Step 2302).

Then, targetCluster.type is evaluated as to whether it is leaf or not (Step 2303). When it is leaf, the following process is repeated until gene information corresponding to leaf is completely compared with the keyword read out from the keyword dictionary file. In other words, the process is repeated until i becomes key_num (Step 2304). First, the attribute of gene information structure gene_info corresponding to targetClust.geneID is evaluated as to inclusion of keyword search[i].keyword (Step 2305). If the keyword is included, search[i].times, which indicates the number of detection of the keyword (search[i].keyword) in the subtree, is increased by 1. Then, leafNo of the detected location is registered in search[i].place indicating the index of the detected location in the subtree (Step 2307). The counter i for keyword search is increased by 1 and the process returns to Step 2304. When i becomes key_num at Step 2304, i.e., when entire keywords are completely compared, leafNo as an index of the subtree is increased by 1 (Step 2309) and the process is ended.

When targetCluster.type is not leaf at Step 2303, a child node is traced. First, targetClust.left is substituted for clustNo (Step 2310), and the keyword searching process (Process A) is performed on left child node using clustNo and leftNo as arguments (Step 2311). When targetCluster.type is icon, targetCluster.right has no child node (Step 2312) and thus the process is ended. When targetCluster.type is not icon at Step 2312, the cluster is of a node type. Thus, targetClust.right is substituted for clustNo (Step 2313), and keyword searching process (Process A) is repeated on the right child node using clustNo and leafNo as arguments (Step 2314) and the process is ended.

Figure 24:
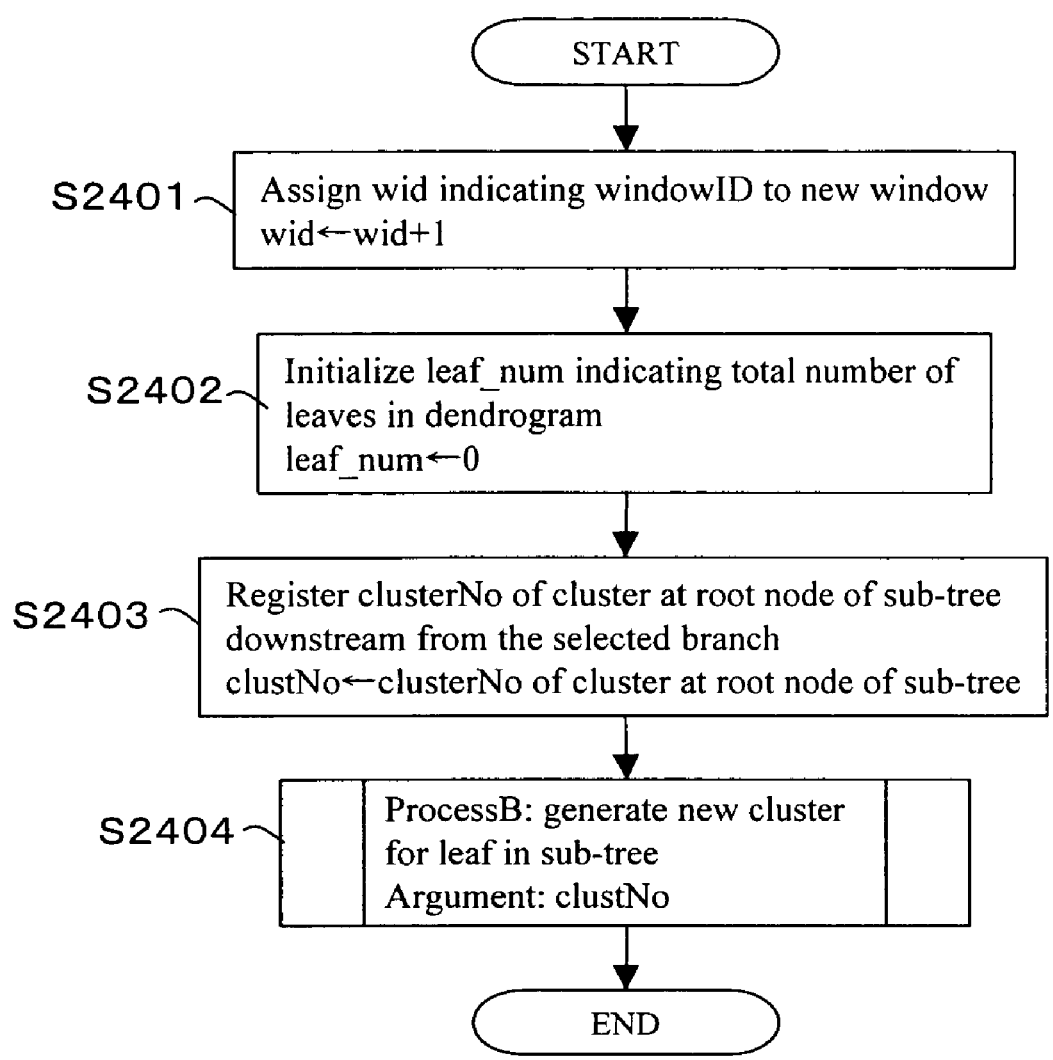
FIG. 24 is a flowchart showing a process of reading out gene data of a subtree.

FIG. 24 is a detailed flowchart of process 1715 in FIG. 17, for reading out gene data of the subtree.

Since a subtree is newly read out and a window is newly generated, wid indicating a new window ID is increased by 1 (Step 2401). In addition, leaf_num indicating the total number of leaves in the dendrogram is initialized to 0 (Step 2402). Then, clusterNo of a cluster at the root node of the subtree downstream from the selected branch is substituted for clusterNo (Step 2403). Finally, process of generating new cluster (Process B) is performed on the leaf-type cluster of the subtree (Step 2404). For this process, clustNo indicating the present cluster is given as an argument. This process will be described later in detail. After reading out all leaves and generating all clusters corresponding to the leaves, the process is ended.

Figure 25:
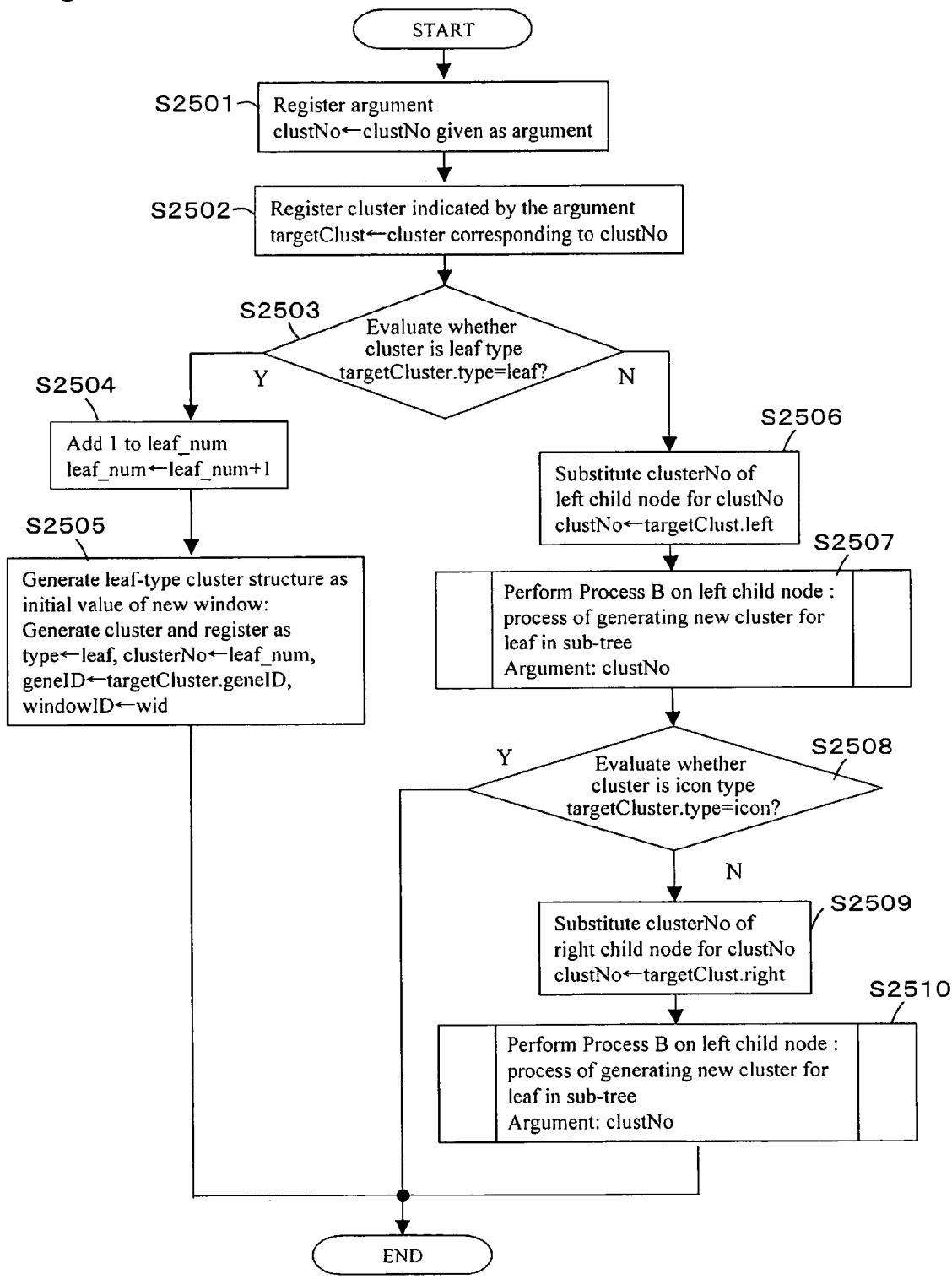
FIG. 25 is a flowchart showing a process of generating a new cluster for a leaf of a subtree (Process B).

FIG. 25 is a detailed flowchart of process 2404 in FIG. 24, for generating a new cluster corresponding to a leaf in the subtree.

The given argument clustNo is registered as clustNo, and the cluster indicated by the given clustNo is set as targetClust (Steps 2501 and 2502). Then, targetCluster.type is evaluated as to whether it is leaf or not (Step 2503). If it is leaf, leaf_num as a counter of the number of leaves of the subtree is increased by 1 (Step 2504). Then, a leaf-type cluster structure is generated as an initial value of the new window. Specifically, a cluster is generated where type, clusterNo, geneID and windowID are set to leaf, leaf_num, targetCluster.geneID and wid, respectively, thereby ending the process (Step 2505).

When targetCluster.type is not leaf at Step 2503, a child node is traced. First, targetClust.left is substituted for clustNo (Step 2506), and a cluster is newly generated again using clustNo as an argument (Process B) (Step 2507). When targetcluster.type is icon, targetCluster.right has no child node, and thus the process is ended (Step 2508). When targetcluster.type is not icon at Step 2508, the cluster is of a node type. Accordingly, targetClust.right is substituted for clustNo (Step 2509), and a new cluster generating process (Process B) is repeated for the right child node using clustNo as an argument and the process is ended (Step 2510).

Herein, the result of the analysis is displayed only on a display device. However, the results can be printed out with a multicolor printer. According to the present invention, the idea of display also comprises a printed out display.

According to the present invention, a method for aiding gene expression analysis or the like is provided, where various clustering methods can be applied to a dendrogram, and a subtree can be replaced with an icon or displayed on a separate window.

What is claimed is:

1. A program embedded in a computer readable medium for displaying a dendrogram comprising:

a module for clustering a plurality of biopolymers with a first clustering method which is based on a set of gene expression data obtained by experiments on the plurality of biopolymers, and displaying clustering results thereof in a form of a dendrogram that is clustered based upon gene expression data of individual biopolymers in a display window;

a module for selecting a subtree in the dendrogram in the display window;

a module for displaying the selected subtree in the dendrogram in a separate display window thereby allowing a user to see in the separate display window more details of the selected subtree;

a module for grouping biopolymers in the selected subtree in the separate display window into at least one function group sharing one of functional characteristics consisting of enzymatic, metabolic, transporting, and cell cycle functions; and a module for displaying said function group of biopolymers in the separate display window thereby confirming by the user that said function group in the selected subtree shares said one of functional characteristics consisting of enzymatic, metabolic, transporting, and cell cycle functions.

2. A program embedded in a computer readable medium for displaying a dendrogram according to claim 1, further comprising:
a module for designating a second clustering method, which is different from the first clustering method, for further clustering the biopolymers in the selected subtree in the separate display window.

3. A program embedded in a computer readable medium for displaying a dendrogram comprising:
a module for clustering a plurality of biopolymers based on a set of gene expression data obtained by experiments on the plurality of biopolymers, and displaying clustering results thereof in a form of a dendrogram that is clustered based upon gene expression data of individual biopolymers in a display window;
a module for selecting a subtree in the dendrogram in the display window;
a module for replacing the selected subtree in the dendrogram with an icon thereby displaying the dendrogram with the icon as a simplified presentation rather than with the selected subtree;
a module for grouping biopolymers in the simplified presentation in the display window into at least one function group sharing one of functional characteristics consisting of enzymatic, metabolic, transporting, and cell cycle functions; and
a module for displaying said function group of biopolymers in the simplified presentation in the display window thereby confirming by a user that said function group in the selected subtree shares said one of functional characteristics consisting of enzymatic, metabolic, transporting, and cell cycle functions.

4. A program embedded in a computer readable medium for displaying a dendrogram according to claim 3, further comprising a module for restoring the selected subtree back from the replacing icon in the dendrogram in the display window.

5. A program embedded in a computer readable medium for displaying a dendrogram comprising:
a module for clustering a plurality of biopolymers based on a set of gene expression data obtained by experiments on the plurality of biopolymers, and displaying clustering results thereof in a form of a dendrogram in a display window;
a module for selecting a subtree in the dendrogram in the display window;
a module for searching within respective information of biopolymers contained in the selected subtree for keywords available in a keyword dictionary file; and
a module for counting biopolymers in the selected subtree whose respective information contains at least one of the searched keywords and displaying each of the searched keywords with a corresponding count of the biopolymers whose respective information contains at least one of the searched keywords;
a module for grouping biopolymers in the selected subtree into at least one function group sharing one of functional characteristics consisting of enzymatic metabolic, transporting, and cell cycle functions;
a module for displaying said function group of biopolymers in the display window; and
a module for displaying the searched keywords available in the selected subtree and said count in a separated display window on top of the display window displaying said function group of biopolymers therein;
a module for highlighting in the display window a location of each of the biopolymers in the selected subtree whose respective information contains the searched keywords;
a module for displaying the highlighted keywords together with said function group of biopolymers in the selected subtree thereby confirming by a user that biopolymers sharing said one of said functional characteristics are grouped in the selected subtree,
wherein said respective information includes a unique nucleotide sequence identifier and a description of a corresponding nucleotide sequence, said description includes a source organism, a gene name/protein name, or a function.

6. A program embedded in a computer readable medium for displaying a dendrogram comprising:
a module for clustering a plurality of biopolymers based on a set of gene expression data obtained by experiments on the plurality of biopolymers, and displaying clustering results thereof in a form of a dendrogram in a display window;
a module for selecting a subtree in the dendrogram in the display window;
a module for designating at least one keyword from a keyword dictionary file;
a module for searching within respective information of biopolymers contained in the selected subtree for biopolymers whose respective information contains the designated keyword; and
a module for highlighting in the display window a location of each of the biopolymers in the selected subtree whose respective information contains the designated keyword;
a module for grouping biopolymers in the selected subtree into at least one function group sharing one of functional characteristics consisting of enzymatic, metabolic, transporting, and cell cycle functions;
a module for displaying the highlighted keywords together with said function group of biopolymers in the selected subtree in the display window thereby confirming by a user that biopolymers sharing said one of said functional characteristics are grouped in the selected subtree,
wherein said respective information includes a unique nucleotide sequence identifier and a description of a corresponding nucleotide sequence, said description includes a source organism, a gene name/protein name, or a function.

7. A program embedded in a computer readable medium for displaying a dendrogram according to any one of claims 1 to 6, wherein the biopolymers are cDNAs, RNAs, DNA fragments or genes.

8. A computer-implemented system for displaying a dendrogram comprising:
a clustering processor for clustering a plurality of biopolymers based on a set of gene expression data obtained by experiments on the plurality of biopolymers, and analyzing and displaying clustering results thereof in a form of a dendrogram in a display window;
a display system for displaying the dendrogram, for displaying on a separate window a subtree selected by a user in the display window thereby allowing the user to see in the separate display window more details of the selected subtree, for grouping biopolymers in the selected subtree in the separate display window into at least one function group sharing one of functional characteristics consisting of enzymatic, metabolic, transporting, and cell cycle functions, and for displaying said function group of biopolymers in the separate display window thereby confirming by the user that said function group in the selected subtree shares said one of functional characteristics consisting of enzymatic, metabolic, transporting, and cell cycle functions; and a keyword dictionary file for storing keywords of respective information associated with each of the plurality of biopolymers, said respective information including a unique nucleotide sequence identifier and a description of a corresponding nucleotide sequence, said description includes a source organism, a gene name/protein name, or a function.

9. A computer-implemented system for displaying a dendrogram according to claim 8, further comprising input means for selecting the subtree by the user.

10. A computer-implemented system for displaying a dendrogram according to claim 8, further comprising means for designating a different clustering method for said grouping biopolymers in the selected subtree displayed on the separate window to secondarily cluster biopolymers included in the subtree, wherein the display system displays secondarily clustered biopolymers in the selected subtree in a form of a dendrogram.

11. A computer-implemented system for displaying a dendrogram according to any one of claims 8 to 10, further comprising means for replacing the selected subtree with an icon as a simplified presentation, and means for restoring the selected subtree back from the replacing icon in the dendrogram in the display window.

12. A computer-implemented system for displaying a dendrogram according to any one of claims 8 to 10, further comprising means for designating keywords from the keyword dictionary file, means for searching within respective information of biopolymers contained in the selected subtree for biopolymers whose respective information contains at least one of the designated keywords, means for counting biopolymers in the subtree whose respective information contains at least one of the designated keywords, wherein the display system displays each of the designated keywords with a corresponding count of the biopolymers whose respective information contains at least one of the designated keywords, and highlights a location of each of the biopolymers in the selected subtree whose respective information contains at least one of the designated keywords thereby confirming biopolymers sharing said one of said functional characteristics are grouped in the selected subtree.

13. A computer-implemented system for displaying a dendrogram according to any one of claims 8 to 10, wherein the biopolymers are cDNAs, RNAs, DNA fragments or genes.

14. A program embedded in a computer readable medium for displaying a dendrogram according to claim 5, wherein the counting module involves counting biopolymers in the selected subtree whose respective information contains synonyms of said one of the selected keywords.

15. A computer-implemented system for displaying a dendrogram according to claim 12, wherein the means for counting counts biopolymers in the selected subtree whose respective information contains synonyms of each of the designated keywords.

* * * * *